United States Patent [19]

Moriya

[11] Patent Number: 5,102,918

[45] Date of Patent: Apr. 7, 1992

[54] PROCESS FOR PRODUCING MODIFIED ORGANIC POLYISOCYANATE

[75] Inventor: Kiyoshi Moriya, Yokohama, Japan

[73] Assignee: Nippon Polyurethane Industry Co., Ltd., Tokyo, Japan

[21] Appl. No.: 640,421

[22] PCT Filed: May 16, 1990

[86] PCT No.: PCT/JP90/00618

§ 371 Date: Jan. 9, 1991

§ 102(e) Date: Jan. 9, 1991

[87] PCT Pub. No.: WO90/14372

PCT Pub. Date: Nov. 29, 1990

[30] Foreign Application Priority Data

May 16, 1989 [JP] Japan .................. 1-120299
Jun. 16, 1989 [JP] Japan .................. 1-152255
Jun. 23, 1989 [JP] Japan .................. 1-159642

[51] Int. Cl.⁵ ............................................ C08G 18/14
[52] U.S. Cl. ...................... 521/110; 521/112; 521/118; 521/125; 521/128; 521/129; 521/131; 521/159; 521/160; 521/161; 544/180; 544/193

[58] Field of Search ............... 521/110, 112, 118, 125, 521/128, 129, 131, 159, 160, 161; 544/180, 193

[56] References Cited

U.S. PATENT DOCUMENTS 4,412,073 10/1983 Robin ...................... 544/193
4,454,317 6/1984 Disteldorf ................ 544/193
4,499,253 2/1985 Kerimis ................... 528/45
4,537,961 8/1985 Robin ...................... 544/193

FOREIGN PATENT DOCUMENTS 5432490 11/1980 Japan .

Primary Examiner—Maurice J. Welsh
Attorney, Agent, or Firm—Davis, Hoixe, Faithfull & Hapgood

[57] ABSTRACT

A modified organic polyisocyanate is prepared in such a manner that a trimerization catalyst, an organic phosphite estr, and a surfactant, and optionally a ferrocene compound are added to an organic isocyanate and/or a partially urethanized organic polyisocyanate to cause isocyanuration in an extent that not more than 20% by weight of entire isocyanate groups are isocyanurated; and a stopper is added, if necessary.

93 Claims, No Drawings

PROCESS FOR PRODUCING MODIFIED ORGANIC POLYISOCYANATE

TECHNICAL FIELD

The present invention relates to a modified organic polyisocyanate having an isocyauurate ring, more particularly to a process for producing a modified organic polyisocyanate which is readily producible, being in a liquid state, superior in compatibility with other resins, and stable, and has an isocyanurate ring. Further, the present invention relates to a process for producing a modified polymethylenepolyphenylpolyisocyanate, a storable resin composition and a foam prepared from the same, and more particularly to a process for producing a modified polymethylenepolyphenyl polyisocyanate having an isocyanurate ring, a storable resin composition prepared from the modified product and a polyol, and a process for producing therefrom a polyisocyananurate foam having low smoking property.

TECHNICAL BACKGROUND

Organic polyisocyanates are utilized hitherto for various applications as foams, elastomers, paints, adhesives and the like by the reaction with active hydrogen compounds.

Such an organic polyisocyanate can also be used by the modification to a polyisocyanate compound having an isocyanurate ring.

The product prepared by reaction of the modified polyisocyanate compound with an active hydrogen compound has heat resistance, flame resistance, rigidity, toughness and the like which are characteristic of isocyanurates, and is utilized in applications where such properties are required.

Accordingly, a variety of isocyanuration polymerization is conducted for isocyanuration of organic polyisocyanates. (The term "isocyanuration" means hereinafter a trimerization of an isocyanate compound to form an isocyanurate ring.) For example, Japanese Patent Laid-open Publications Sho. 54-32490 and Sho. 52-69497 respectively describe methods for the isocyanuration by use of a catalyst such as a metal salt of acetylacetone, an alkali metal salt of an organic acid, and the like. These production processes are not satisfactory, because the selectivity of the catalyst is very narrow for the organic polyisocyanate; and particularly in the isocyanuration polymerization, an organic isocyanate in which the difference between the reactivities of the first and the second isocyanate groups is little like those in diphenylmethane diisocyanate is liable to polymerize to become viscous and to give a partially non-uniform product having a low isocyanate content and low compatibility with other resins.

Further, upon carrying inactivation of the catalyst in order to improve stability of the modified polyisocyanate, if the reaction is conducted without a solvent insoluble precipitate tends to be formed and it is difficult to control the isocyanuration reaction, so that it is not satisfactory industrially and improvement thereof has been desired. In other words, a modified organic polyisocyanate having an isocyanurate ring has been desired which is prepared readily through isocyanuration of an organic polyisocyanate, and which is stable in storage, and excellent in compatibility to other resins.

Heretofore, the preparation of a polyisocyanurate foam having flame resistance and low smoking property has been carried out in the presence of a trimerization catalyst upon a reaction of a polyisocyanate with an active hydrogen compound. However, further improvement of the properties are desired.

A polymethylenepolyphenyl-polyisocyanate (hereinafter referred to as "polymeric MDI") exhibits heat resistance based on its characteristic feature when reacted with polyols.

Polymeric MDI solely or a polyol adduct of polymeric MDI is used nowadays. However, polyol adducts are liable to deteriorate by heat, and are limited in use for flame-resistant foams.

Polyisocyanurate foams are widely used for heat insulating materials, light-weight structural materials, and sound absorption materials because of their superior characteristics. The introduction of the isocyanurate ring into polyurethane crossliking makes heat resistance, hydrolysis resistance, and dimension stability higher. However, the application fields thereof is limited because of an increase of a smoking quantity in combustion on heating to a high temperature.

For the improvement of the disadvantage, an additive such as ammonium polyphosphate, a phosphate ester, p-nitroaniline sulfonic acid, and the like is added to accelerate carbonization of foam on contact with flame to reduce the smoking quantity.

Further, as a method for lowering the smoking properties attributed to control of combustibility by addition of a heat-resistant inorganic powder, for example, addition of calcium carbonate, ammonium phosphate, ammonium sulfate, and the like is tried to dilute a combustible gas generated from the foam with an inert gas ($CO_2$, $NH_3$, etc.) generated by pyrolysis of the inorganic powder and to lower combustibility by depression of combustion.

However, since such an additive is required to be added in a large amount, these methods have disadvantages lowering storage stability of reaction mixing liquid component and mechanical properties of the foam.

Further, for imparting high flame resistance to a foam, the concentration of isocyanurate rings in formulation containing a polyisocyanate and a polyol is increased by raising the index (NCO/OH molar ratio) to make the concentration of isocyanurate linkage in the foam high so as to possess heat resistance and flame resistance derived from the isocyanurate linkage. The raising of the NCO/OH ratio, however, is limited because an excessively high ratio leads to a large amount of unreacted isocyanate group contained, resulting in disadvantages of increased smoking in combustion and explosive breakage upon contact with flame, and the foam thus prepared has considerable brittleness coming from the characteristic property of isocyanurate linkage at the same time. Accordingly, sufficient properties are not attained as an semi-incombustible material, and further improvement has been desired. That is, it has been desired to improve the modified polyisocyanate for polyisocyanurate foams, and flame resistance, smoking property, friability, heat resistance, compatibility with resins, etc. for polyisocyanurate foam produced from the polyisocyanate, a polyol, a blowing agent, an additive, etc. upon using as incombustible materials.

The inventors have found after comprehensive investigation that a modified organic polyisocyanate which contains an isocyanurate ring is effectively produced by addition of an organic polyisocyanate trimerization catalyst, a specific additive, optionally a ferrocene compound, etc., and completed the present invention.

The inventors of the present invention has also succeeded in isocyanuration of a polymeric MDI after comprehensive investigation, and also found that the foam prepared by using the isocyanate is highly superior in incombustibility, low smoking property, low friability, etc., and completed the present invention.

DISCLOSURE OF THE INVENTION

The present invention provides a process for producing a modified organic polyisocyanate having an isocyanurate ring, characterized in that a trimerization catalyst, an organic phosphite ester, and a surfactant, and optionally a ferrocene compound are added to an organic polyisocyanate and/or a partially urethanized organic polyisocyanate to cause isocyanuration of not more than 20% by weight of entire isocyanate groups; and, if necessary, a stopper is added.

The present invention also provides a modified polymethylenepolyphenyl-polyisocyanate, characterized in that the modified polymethylenepolyphenyl-polyisocyanate is prepared by reaction in which a trimerization catalyst and an organic phosphite ester are added to a polymethylenepolyphenyl-polyisocyanate or a partially urethanized polyisocyanate prepared by reacting the polymethylenepolyphenyl-polyisocyanate with a polyol having a molecular weight of from 62 to 1000.

The present invention further provides a resin composition for foam, comprising the resulting modified product, a polyol having a molecular weight of not less than 200, a blowing agent, a catalyst, a foam stabilizer, optionally a filler, and the like.

The present invention still further provides a process for producing a polyisocyanurate foam, characterized by foaming by use of the resulting resin composition.

DETAILED DESCRIPTION OF THE INVENTION

The present invention is described in detail below.

The organic polyisocyanate used in the present invention is exemplified by
2,4- or 4,4'-diisocyanatodiphenyl ether,
2,4- or 2,6-toluene diisocyanate,
4,6-dimethyl-1,3-phenylene diisocyanate,
4,4'-diisocyanatodibenzyl,
9,10-anthracene diisocyanate,
3,3'-dimethyl-4,4'-diisocyanatodiphenylmethane,
2,6'-dimethyl-4,4'-diisocyanatodiphenyl, xylylene diisocyanate,
2,4- or 4,4'-diphenylmethane diisocyanate,
and the like.

Particularly useful organic polyisocyanates in the present invention are the aromatic polyisocyanate, namely polymethylenepolyphenyl polyisocyanates, represented by the general formula (1):

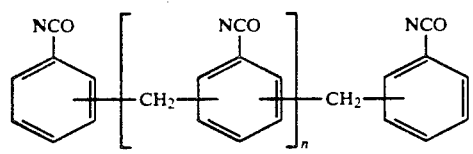

where n=0-8; and mixtures containing the above polyisocyanates.

The partially urethanized organic polyisocyanate used in the present invention is a product of urethanizing reaction of an organic polyisocyanate and a hydroxyl-group-containing compound, and can be prepared by adding a hydroxyl-group-containing compound to an organic polyisocyanate at a reaction temperature of not more than 100° C. preferably from 60° to 90° C. for approximately 2 hours in a conventional manner. If the temperature is above 100° C., a side reaction occurs which causes extremely high viscosity of the product of the trimerization reaction, sometimes resulting in formation of a gel-like matter. The urethane groups thus introduced exhibit a cocatalytic effect which allows the isocyanuration reaction to proceed readily. This is considered to be due to the remarkable activation of isocyanate group resulting from formation of hydrogen bonding between the active hydrogen in the urethane group and the oxygen atom in the isocyanate group. Thus, the cocatalytic effect of the urethane group makes it possible to decrease the amount of addition of the catalyst. Since the increase of the concentration of urethane groups reduces the characteristic heat stability of the isocyanurate ring formed later, the urethane group concentration need to be adjusted depending on the purpose. In the present invention, the urethanizing ratio is desirably not more than 10% by weight of the entire isocyanate groups.

The hydroxyl-group-containing compound to be used for urethanizing reaction has preferably a molecular weight of not higher than 2000, more preferably not higher than 1000, and has a functionality of not less than 3.

The examples are primary alcohols represented by the general formula: R'OH, where R' is alkyl, arylalkyl, alkylaryl, aryl, and alkenyl: such as 2-ethylhexyl alcohol, lauryl alcohol, nonyl alcohol, and the like. Other examples are diols such as ethylene glycol, diethylene glycol, 1,3-butanediol, 1,4-butanediol, propylene glycol, dipropylene glycol, neopentyl glycol, 1,6-hexane glycol, 2-ethylhexanediol, 2,2,4-trimethylpentanediol, and the like, and polyesterdiols, polyetherdiols, and the like. Further examples are triols including trihydric alcohols such as trimethylolethane, trimethylolpropane, glycerin, and the like, and polyester- and polyetherpolyols, and the like. These are used solely or as a mixture of the two or more thereof in an arbitrary ratio. The urethanizing reaction and the isocyanurating reaction may be conducted in the presence of, or in the absence of a solvent.

The modified polymethylenepolyphenyl-polyisocyanate according to the present invention is prepared favorably by conducting isocyanuration reaction of a polymethylenepolyphenyl-polyisocyanate or a polyol adduct of the polyisocyanate in the presence of an alkali metal salt or a tertiary amine solely or in combination thereof as the catalyst and additionally an organic phosphite ester at a temperature of not higher than 100° C., preferably from 20° to 70° C.

The catalyst used for isocyanuration modification of the present invention includes alkali metal salts of carboxylic acids having 2-12 carbons; and phenolates and alcoholates such as potassium phenolate, sodium methoxide and the like. Particularly effective are amine series compounds such as 2,4,6-tris(dimethylaminomethyl)phenol, 2,4-bis(dimethylaminomethyl)phenol, 2,6-di-tertiary-butyl-4-dimethylaminotrimethylsilanephenol, triethylamine, N,N',N''-tris(dimethylaminopropyl)hexahydrotriazine, diazabicycloundecene, and the like.

The organic phosphite ester per se used in the present invention does not catalyze the isocyanuration. However, the combined use thereof with a trimerization catalyst makes the control of isocyanuration reaction easy, and gives a stable modified polymethylenepolyphenylpolyisocyanate without generating turbidity in the reaction product.

The organic phosphite ester used in the present invention includes organic phosphite diesters and organic phosphite triesters.

These compounds have from one to four of the partial structure of

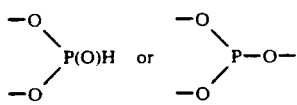

(in which one bond of the oxygen atoms is linked to a carbon atom). In the present invention, the organic phosphite triester includes tris($\beta$-chloropropyl) phosphate, and the like. The organic phosphite diester includes the compounds represented by $(RO)_2P(O)H$ (where R may be the same or different and is an alkyl having 1-20 carbons or an aryl such as phenyl which may be substituted by an alkyl of 1-20 carbons). Such diester is exemplified by dilauryl hydrogen phosphite, diphenyl hydrogen phosphite, and the like. The alkyl represented by the symbol R may be partially substituted by a halogen such as chlorine, for example, tris(2,3-dichloropropyl) phosphite. The oxygen atom in the phosphite may be substituted by a sulfur atom. For example, such compound is exemplified by trilauryl trithiophosphate, and the like.

The compounds represented by $(R-O-)_3P$ (where R may be the same or different and is an alkyl having 1-20 carbons or an aryl such as phenyl which may be substituted by an alkyl of 1-20 carbons) include monophosphites such as triethyl phosphite, tributyl phosphite, tris(2-ethylhexyl) phosphite, tridecyl phosphite, trilauryl phosphite, tris(tridecyl) phosphite, tristearyl phosphite, triphenyl phosphite, tris(nonylphenyl) phosphite, tris(2,4-di-t-butylphenyl) phosphite, and the like.

Further, the following compounds can be exemplified: di-, tri- or tetra-phosphite derived from polyhydric alcohol, such as distearyl pentaerythrityl diphosphite, ditridecyl pentaerythritol diphosphite, dinonylphenyl pentaerythritol diphosphite, tetraphenyl tetratridecyl pentaerythritol tetraphosphite, tetraphenyl dipropylene glycol diphosphite, tripentaerythritol triphosphite, and the like; diphosphites, derived from a bisphenol series compounds, such as dialkyl (1-20 carbons) bisphenol A diphosphite, 4,4'-butylidenebis (3-methyl-6,6-butylphenyl-ditridecyl) phosphite, and the like; and polyphosphites such as hydrogenated bisphenol A phosphite polymer (molecular weight: 2400-3000), and the like.

In the present invention, such an organic phosphite ester is used in combination with the catalyst, and the amount of the catalyst may be less than the most effective amount in single use of the catalyst.

The catalyst is used in an amount ranging from 0.005 to 0.5% by weight based on the starting isocyanate compound, which depends on the activity of the catalyst. The phosphite ester is used in an amount of from approximately 1/10 to 20 times of the catalyst.

The reaction rate of the isocyanuration is strongly affected by the initial concentration dependency of the catalyst. In particular, upon using diphenylmethane diisocyanate, in isocyanuration in a conventional manner, gel-like matter is formed and suspends non-uniformly, and occasionally gelation occurs.

Accordingly, in order to reduce the initial concentration dependency of the catalyst, it is preferable to apply a method in which the catalyst is added in a low initial concentration by addition of a diluent etc. The diluent is preferably a compound inactive to the isocyanate and incombustible to keep the fire resistance and the heat resistance of a polymer to be produced. The examples are methylene chloride, trichlorofluoromethane, dichlorodifluoromethane, dichlorotetrafluoroethane, trichlorotrifluoroethane, and the like.

By using such a catalyst and conducting the partial polymerization to an extent that not more than 20% by weight of the entire isocyanate groups react, a liquid and stable polymer can be obtained. In modifying an organic polyisocyanate by isocyanuration, since the isocyanuration-modified matter does not have sufficient compatibility with the organic polyisocyanate, urethane groups are introduced for improvement of the compatibility. In the present invention, by using a surfactant, isocyanuration modification is achievable in the absence of a solvent both for organic polyisocyanates and for partially urethanized organic polyisocyanates, giving a liquid and stable isocyanuration-modified product free from turbidity and containing scarcely a polymer of high molecular weight. The use of a surfactant improves the compatibility of the resulting isocyanuration-modified product with other resins, so that the curing reaction with an active-hydrogen-containing compound to be reacted with an isocyanate group will proceed smoothly, and the physical properties of the resulting cured product will be improved.

In the present invention, the surfactant may be added either in the initial stage or in a later stage of the reaction.

The surfactant used in the present invention is manufactured, for example, by condensing a polyglycol ether, which is derived by reacting an alkylene oxide such as ethylene oxide, propylene oxide, butylene oxide, etc., preferably ethylene oxide with polyethylene glycol or polypropylene glycol, with an organic compound having one reactive hydrogen atom. Such a compound having one reactive hydrogen atom includes alcohols, phenols, thiols, and primary and secondary amines. The surfactant may be a nonionic surfactant prepared from a polyglycol ether and a carboxylic acid, a sulfonic acid, or an amide thereof. The surfactant may be a polyethylene glycol ether. Further, the surfactant includes polyalkylene oxide derivatives prepared from the polyglycol ether and a phenol compound having one or more alkyl substituents, including polyethylene glycol nonylphenyl ether.

Further the surfactant includes those called Pluronic type, for example. These surfactants are prepared generally by use of butylene oxide, amylene oxide, phenylethylene oxide, cyclohexene oxide, propylene oxide or a mixture thereof; for example, such surfactant can be prepared by polymerizing 1,2-alkylene oxide or a substituted alkylene oxide in the presence of an alkali catalyst to give a corresponding water-insoluble polyalkylene glycol and subsequently condensing with required moles of ethylene oxide. The examples are Pluronic L-61, and Pluronic L-62 (made by Asahi Denka Kogyo K.K.). The surfactant further includes nonionic surfactant, for example, prepared by forming an aldehyde by catalytic reaction of a polyolefin such as tripropylene, tetrapropylene, pentapropylene, diisobutylene, triisobutylene, tetrabutylene, propylene-isobutylene, and tributene with carbon monoxide and hydrogen, then reducing the resulting aldehyde into an alcohol, and reacting the alcohol with a required amount of ethylene oxide. The examples are polyoxyethylene alkyl ethers, such as polyoxyethylene lauryl ether, polyoxyethylene oleyl ether, and the like.

Further, particularly effective surfactants in the present invention are those represented by the general formula (2):

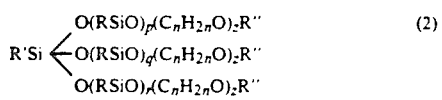

where R, R', and R" are respectively an alkyl group having 1-20 carbons; p, q, and r are respectively an integer of 1 or more; n is an integer of 2-4; and z is an integer of 5 or more. The examples are silicone surfactants such as L-5340 (made by U.C.C.), Toray Silicone SH193 (made by Toray Industries, Inc.), B8404 (made by Goldschmidt Co.), and the like. Such a surfactant is used in an amount of 0.1 to 2% by weight based on the organic polyisocyanate.

The modification reaction by isocyanuration according to the present invention is conducted at a reaction temperature of not higher than 100° C., preferably in the range of 15° to 70° C. In the reaction, the use of the surfactant allows the isocyanuration reaction to proceed effectively at a relatively low temperature, giving a stable and liquid isocyanuration-modified product because of uniform dispersion of the resulting isocyanuration-modified product in the reaction product and gradual progress of the reaction.

An excessive amount of the catalyst or the reaction temperature exceeding 100° C. tends to generate a polymer of an isocyanurate compound or a polymer of an allophanate compound, which may decrease the compatibility, or cause gelation.

The substance which has a linear structure containing a ferrocene skeleton in the main chain and is useful for the isocyanuration-modification of the present invention is represented by the following general formula (1)

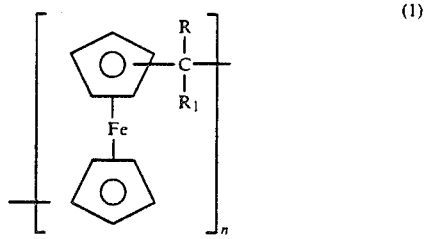

where R and $R_1$ may be mutually the same or different, and are hydrogen, alkyl, alkenyl, arylalkyl, or aryl, respectively, and may form a ring together with the carbon atom of —C(R)(R')—; and n is 0, or 1 or more. The position of the substitution in the ferrocene nucleus is 1,2-, 1,3-, or 1,1'-, or a mixture thereof. Otherwise, the substance may be a mixture of a linear structure having a ferrocene skeleton containing an unreacted ferrocene.

The useful ferrocene compounds include mono- and di-lower alkyl ($C_{1-8}$) dicyclopentadienyl iron compounds such as ethyldicyclopentadienyl iron, n-butyldicyclopentadieneyl iron, diethyldicyclopentadieneyl iron, n-butyldicyclopentadieneyl iron; and dimer and polymeric reaction products of dicyclopentadieneyl iron or a derivative thereof, in which the substituent is a lower alkyl ($C_{1-8}$), with an aldehyde or a ketone such as 2,2-di(ethyldicyclopentadienyl iron)-propane, di(-butylcyclopentadienyl iron)-propane, di(cyclopentedienyl iron)-methane, and the like.

The amount of the ferrocene compound to be used in the present invention is in the range of from 0.05 to 0.4%, preferably 0.08 to 0.3% by weight based on the organic polyisocyanate as the starting material.

For producing the modified organic polyisocyanate, the reaction time, the yield and quality of the modified product, etc. may be adjusted effectively by the kind and the amount of the catalyst to be used. Accordingly, the NCO content and the viscosity of the modified organic polyisocyanate can be adjusted arbitrarily by the NCO content at the termination of the reaction since it can be measured by a known conventional titration analysis.

Thus, the isocyanuration of the present invention is advantageous in decreased amount of the catalyst, the possibility of the reaction at a low-temperature in a short time, and so on.

An acidic compound may be used as a terminating agent, if necessary, in the production of the isocyanurated organic polyisocyanate according to the present invention. The acidic compound is exemplified by hydrochloric acid, phosphoric acid, dimethyl phosphate, trimethyl phosphate, triethyl phosphate, tricresyl phosphate, tripheryl phosphate, tributyl phosphate, p-toluenesulfonic acid, methyl p-toluenesulfonate, xylenesulfonic acid, benzenesulfonic acid, methanesulfonic acid, alkylbenzenesulfonic acids, dinaphthalenedisulfonic acid, dinaphthalenemonosulfonic acid, dinonylnaphthalenedisulfonic acid, dinonylnaphthalenemonosulfonic acid, benzoyl chloride, acetyl chloride, and analogous compounds thereof.

The amount of the stopper to be used is in the range of from 0.3 to 5 equivalents, preferably from 1.0 to 2.0 equivalents based on the catalyst. The addition thereof during the isocyanuration reaction promotes the stabilization of the modified organic polyisocyanate without causing turbidity of the reaction liquid.

The modified organic polyisocyanate produced according to the present invention contains a surfactant, an organic phosphite ester, and a ferrocene compound. When flames are applied to the resin obtained by the reaction of the modified organic polyisocyanate and an active hydrogen containing compound, it is assumed that, owing to the presence of a iron compound coming from the ferrocene compound having strong oxidizing action, the side chains of the resin are rapidly oxidized and the main chain of the resin is carbonized to form a carbon polymer, which gives to the resin superior heat resistance and oxidation resistance, and decreases the combustion velocity, thus resulting in the incombustibility and low smoking properties.

Accordingly, a urethane-modified isocyanurate foam having a higher NCO/OH equivalent ratio (index) has improved heat resistance and improved flame resistance because the iron compound serves to increase carbonization yield and to decrease the amount of the decomposition gas.

The modified product of the present invention has stable quality even without a solvent, so that it is useful widely not only for plastic foams and elastomers but also as starting materials of paints, adhesives and the like. The products derived from the reaction with an active hydrogen compound exhibit excellent performance in flame retardance, heat resistance, water resistance, toughness, and so on.

Urethane linkage formed from a portion of the polymethylenepolyphenyl-polyisocyanate and a polyol facilitates the isocyanuration, and improves significantly the compatibility of the resulting modified product with other resins. However, the increase of the concentration of the urethane group will prevent the generation of sufficient heat stability which is characteristic of the isocyanurate ring to be formed later, so that the concentration of the urethane group should be selected depending on the use thereof.

A resin composition for polyisocyanurate foam, composed of a combination of a partially isocyanurated modified polymethylenepolyphenyl-polyisocyanate and a polyol having a molecular weight of not less than 200 and having at least two hydroxyl groups in the molecule is superior in flame retardance, heat resistance, low smoking property, low friability, etc., when made into a foam, in comparison with conventional resin compositions for urethane foams.

The partially isocyanurated modified polymethylenepolyphenyl-polyisocyanate in the present invention is a modified polymethylenepolyphenyl-polyisocyanate in which the trimerization forming the isocyanurate ring is carried out in such a way that from 1 to 10% by weight of the entire isocyanate groups are isocyanurated.

There can be present an isocyanurate-group-containing other polymer having higher molecular weight besides the trimer forming the isocyanurate ring of the present invention. Such a high-molecular polyisocyanurate polymer, although it may also be effective in incombustibility and heat resistance, is not preferable because a large amount of the high-molecular polymer will increase viscosity and decrease the compatibility with other resins, and will impair the workability.

The isocyanuration reaction of the present invention is practicable at a low temperature and in a short time, and can be conducted in such a way that 1 to 10% by weight of the entire isocyanate groups turn into an isocyanurate by selection of production conditions. In the present invention, the high-molecular polymer is almost not formed. However, if the reaction conditions deviate from that according to the present invention, a high molecular isocyanurate comes to be contained, which is undesirable because the compatibility of the high molecular substance in particular is low.

In an embodiment, the present invention can use a modified polymethylenepolyphenyl-polyisocyanate having terminal isocyanate groups, which is prepared by isocyanuration of 1% to 10% by weight of the entire isocyanate groups to form a modified product containing a trimer, and by urethanization by the reaction of the resulting modified product with a polyol to cause urethanation.

The polyisocyanurate foam prepared by the reaction of a modified polymethylenepolyphenyl-polyisocyanate which is derived by selecting the ratio of the trimer forming an isocyanurate ring within the range of from 1 to 10% by weight of the entire isocyanate groups with another resin is a foam having incombustibility, heat resistance, low smoking property, low friability, and uniform cell structure. Outside the aforementioned range, the intended characteristics is not obtainable.

The polyol to be reacted with the modified polymethylenepolyphenyl-polyisocyanate or a partially urethanized modified polymethylenepolyphenylpolyisocyanate may be any polyol having a molecular weight of not less than 200, and having at least two hydroxyl groups in the molecule. Typical examples are polyesterpolyols, polyetherpolyols, and the like. These polyols may be used in combination of two or more.

The polyester polyol may be prepared in a conventional manner by reaction of one or more of the compounds having at least two hydroxyl groups such as ethylene glycol, diethylene glycol, trimethylene glycol, 1,2-propylene glycol, 1,3-butanediol, tetramethylene glycol, hexamethylene glycol, decamethylene glycol, glycerin, trimethylol propane, pentaerythritol, sorbitol, bisphenol A, and the like with one or more of the compounds having at least two carboxyl groups such as malonic acid, maleic acid, succinic acid, adipic acid, tartaric acid, pimelic acid, sebacic acid, oxalic acid, phthalic acid, terephthalic acid, azelaic acid, trimellitic acid, glutaconic acid, α-hydromuconic acid, β-hydromuconic acid, α-butyl-α-ethylglutaric acid, α,β-diethylsuccinic acid, hemimellitic acid, 1,4-cyclohexanedicarboxylic acid, and the like.

Further, the polyesterpolyols derived by transesterification between a polyalkylene terephthalate polymer represented by the general formula below and a low molecular diol is useful:

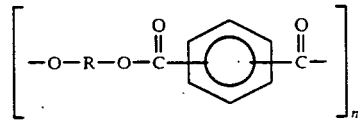

where R is an alkyl having 1 to 10 carbons, and n is a number corresponding to the molecular weight of 1500 or more. The low molecular weight diol here includes ethylene glycol, propylene glycol, diethylene glycol, triethylene glycol, dipropylene glycol, butanediol, glycerol, trimethylolpropane, and the like.

The polyetherpolyols are prepared by addition-polymerizing one or more of monomers such as ethylene oxide, propylene oxide, butylene oxide, amylene oxide, glycidyl ether, methyl glycidyl ether, t-butyl glycidyl ether, phenyl glycidyl ether, and the like in a conventional manner by using as the initiating substance one or more of the compounds having at least two active hydrogen atoms such as ethylene glycol, 1,3-propylene glycol, 1,2-propylene glycol, 1,4-butanediol, 1,3-butanediol, 1,2-butanediol, 1,5-pentane diol, 1,7-heptanediol, glycerin, trimethylolpropane, trimethylolethane, hexane-1,2,6 triol, α-methylglycoside, pentaerythritol, sorbitol, sugar type alcohols like sucrose, glucose, fructose, etc., bisphenol A, ethylenediamine, propylenediamine, diethylenetriamine, toluenediamine, metaphenylenediamine, diphenylmethanediamine, xylenediamine, and the like.

If the molecular weight of the polyol is not higher than 200, the resulting foam is extremely hard and brittle, and does not give sufficiently strong foam properties, which is not suitable for foams.

The resin composition having storage stability of the present invention is obtained by employing a modified polymethylenepolyphenyl-polyisocyanate or a partially urethanized modified product thereof and a polyol at an NCO/OH blending ratio of not less than 2.0. Hitherto a polyisocyanurate foam has been considered not to be produced readily at a high NCO/OH ratio. The causes are the difficulty of uniformly conducting the isocyanuration under the time restriction of respective foaming reaction steps although the urethanizing reaction proceeds rapidly in the presence of a suitable catalyst. Thus, the two different reaction mechanisms do not give satisfactory foam properties. Hence, the selection of the specific catalyst is necessary for proceeding the reactions of the two different mechanisms concurrently and uniformly.

According to the present invention, the urethanizing reaction and the isocyanurating reaction are conducted effectively, concurrently and uniformly even at a high NCO/OH ratio by use of a partially isocyanurated modified polymethylenepolyphenyl-polyisocyanate or a partially urethanized modified polymethylenepolyphenyl-polyisocyanate, and thus a polyisocyanurate foam intended by the present invention is produced which is low smoking, high flame retardant, high heat resistant, and low friability useful as semi-incombustible materials.

Consequently, the use of the modified polymethylenepolyphenyl-polyisocyanate or a partially urethanized modified polymethylenepolyphenyl-polyisocyanate according to the present invention allows a high concentration of isocyanurate rings, and sufficient properties of incombustibility and heat resistance which are characteristic of the isocyanurate ring.

The resin composition having storage stability of the present invention effects isocyanuration reaction selectively in a high yield, and smoothly even at a high NCO/OH ratio, and therefore is highly superior in workability. As the results, it gives a heat resistant foam which contains isocyanurate ring structure in a high concentration, decreases the weight loss at long time of heating at a high temperature, and has heat resistance such that, even when exposed to flame, neither deformation nor crack is found at the back face of the foam and the periphery of the portion subjected to the flame.

The foam prepared from the resin composition having storage stability of the present invention gives a molded product which has high heat resistance, low friability, incombustibility, and excellent physical properties of the foam in addition to the low smoking property. Such properties have not been achieved until now.

In production of polyisocyanurate foam from the reaction of a modified polymethylenepolyphenyl-polyisocyanate or a partially urethanized modified polymethylenpolyphenyl-polyisocyanate with a corresponding polyol, a conventional trimerization catalyst may be used as the catalyst. The examples include alkali metal salts of carboxylic acids having 2 to 12 carbons such as potassium acetate, potassium benzoate, potassium 2-ethylhexanate, potassium naphthenate, and the like; amines such as 2,4,6-tris(dimethylaminomethyl)-phenol, triethylamine, N,N',N''-tris(dimethylaminopropyl)hexahydrotriazine, triethylenediamine, diazabicycloundecene, tetramethylhexanediamine, and the like; and alcoholates and phenolates such as potassium phenolate, sodium methoxide and the like. The combination one or more of the above catalysts or analogous compounds may be used.

The amount of the isocyanuration catalyst upon production of the polyisocyanurate foam is approximately in the range of from about 0.01 to 20% by weight based on the polymethylenepolyphenyl-polyisocyanate or partially urethanized modified polymethylenepolyphenyl-polyisonate.

Any known blowing agent employed in production of urethane foams or isocyanurate foams may be applicable in the present invention. The examples include low-boiling inert solvents such as trichloromonofluoromethane, dichlorodifluoromethane, dichloromonofluoromethane, dichlorotetrafluoroethane, trichlorotrifluoroethane, dibromotetrafluoroethane, methylene chloride, trichloroethane, benzene, toluene, pentane, hexane and the like; substances, which evolve carbon dioxide gas by reaction with an organic polyisocyanate, such as water, crystal-water-containing compounds, aldoximes, and the like; the substances, which evolve a decomposition gas on heating, such as sodium bicarbonate, azoisobutylonitrile, ammonium carbonate, and the like. Among them, trichloromonofluoromethane and water are preferable. The amount of the blowing agent is suitably decided depending on the kind of the blowing agent.

The foam stabilizer used in the present invention may be any of conventional ones including silicone type surfactant such as organopolysiloxanes, organopolysiloxane-polyoxyalkylene copolymers, polyalkenylsiloxanes having a polyoxyalkylene side chain, and the like; and cation type, anion type, and nonion type surfactants. The amount of the foam stabilizer may be decided suitably depending on the kind and properties of the foam stabilizer.

In the present invention, additives such as glass balloons, silica balloons, glass fiber, carbon fiber, other inorganic fillers, and the like, if necessary, may be additively used. Further, a flame-retarding compound such as phosphate esters may be added.

Specifically the polyisocyanurate foam is readily produced from the aforementioned constituents by mixing the constituents homogeneously with any apparatus capable of homogeneous mixing the constituents, such apparatus includes a laboratory small-size mixer or a foaming machine for urethane foam production.

The resin composition of the present invention can prepare with remarkable efficiency polyisocyanurate resins excellent in heat resistance, flame retardance, and the like by use of a two-component reaction pouring machine or an injection molding machine, so that the composition is applicable to construction materials, main exterior shells of audio apparatuses, electric appliance parts, household articles, automobile parts, and the like.

The present invention can prepare a modified organic polyisocyanate having an isocyanurate ring readily and stably in a short time with a small amount of a catalyst.

The modified product produced according to the present invention is a modified organic polyisocyanate which is liquid and stable, and sufficiently compatible with other resins, and has strongly active isocyanate groups at the ends of the molecules. The reaction of the modified organic polyisocyanate with a compound having active hydrogen reactive to the isocyanate group will give a product having flame retardance, heat resistance, and rigidity in good workability.

Further, the organic polyisocyananurate foam produced according to the present invention has excellent flame resistance upon contact with flame. Even when subjected to forced combustion, the foam is not deformed or cracked remarkably, produces less smoke, and is superior in flame retardance, heat resistance, and mechanical properties.

The present invention is described in more detail referring Examples without thereby limiting it in any way.

In the Examples, "parts" and "%" both mean "parts by weight" and "% by weight" respectively unless otherwise mentioned.

EXAMPLE 1

In an 1-liter four-neck flask equipped with a thermometer, a stirrer, and a nitrogen seal tube with ground glass fitting, there were placed 500 parts of Millionate MR-200 (made by Nippon Polyurethane Industry Co., Ltd.) as an organic polyisocyanate, 4.0 parts of L-5340 as a surfactant, 1.0 part of Ankamine K-54 as a catalyst, 5.0 parts of triethyl phosphite as a cocatalyst, and 2.0 parts of R-113 as a diluent. The catalyst was fed as a mixture with the diluent. The air in the flask was replaced by nitrogen. The reaction mixture was stirred and heated to 50° C. After the reaction for 3.5 hours, the NCO content was measured to be 28.6%, and the reaction liquid was found to be a transparent brown liquid. 0.5 part of phosphoric acid was added as a stopper to the reaction liquid, which was stirred at 50° C. for one hour to finish the reaction.

The resulting isocyanurate-modified polyisocyanate was a transparent brown liquid, having an NCO content of 28.6% and a viscosity of 850 cp/25° C., and containing a trimer as observed by infrared absorption spectra. No change was observed after 6 months.

EXAMPLES 2-9

The reactions were conducted similarly as in Example 1 under the conditions shown in Table 1. The results are shown in Table 1 and Table 1-1.

EXAMPLE 10

500 parts of MR-200, and 6.1 parts of 1,3-butanediol as a polyol were placed in the same four-neck flask as used in Example 1. The air in the flask was replaced by nitrogen, and the reaction was allowed to proceed at 60° C. for 2 hours. The NCO content was measured to be 29.4%.

Subsequently, 4.0 parts of L-5340, 0.7 parts of Ankamine K-54 and 2.0 parts of R-113 were mixed and added thereto. 3.0 parts of triethyl phosphite was further added. The mixture was allowed to react at 50° C. for 2.0 hours. The NCO content was determined to be 26.9%. To the reaction liquid, 0.35 parts of phosphoric acid was added, and the liquid was stirred at 50° C. for 1.0 hour to finish the reaction.

The resulting isocyanate-modified product was a transparent brown liquid, having an NCO content of 26.9% and a viscosity of 4500 cp/25° C., and containing a trimer as observed by infrared absorption spectra. No abnormality was observed after storage stability test for 6 months.

EXAMPLES 11-18

The reactions were conducted similarly as in Example 10 under the conditions shown in Table 1. The results are shown in Table 1 and Table 1-1.

COMPARATIVE EXAMPLES 1-3

Comparative example 1 was conducted in a manner similar to that of Example 10, and Comparative examples 2 and 3 were conducted in a manner similar to that of Example 1 of the present invention. The amount of the materials, the reaction conditions and results are shown in Table 1 and Table 1-1.

TABLE 1

| URETHANIZING REACTION | | Example No. 1 | 2 | 3 | 4 | 5 | 6 | 7 | 8 | 9 | 10 | 11 |
|---|---|---|---|---|---|---|---|---|---|---|---|---|
| Isocyanate component | MR-200 (1) | 500 | 500 | 500 | 500 | 500 | 500 | 500 | 500 | 500 | 500 | 500 |
| | T-80 (2) | | | | | | | | | | | |
| | L-5340 (3) | 4.0 | 4.0 | 4.0 | 4.0 | 4.0 | 4.0 | 4.0 | 4.0 | 4.0 | 4.0 | 4.0 |
| Polyol component | 1,3-butanediol | | | | | | | | | | 6.1 | |
| | Diethylene glycol | | | | | | | | | | | 6.9 |
| | PP-200 (4) | | | | | | | | | | | |
| | PEG-400 (5) | | | | | | | | | | | |
| | PP-1000 (6) | | | | | | | | | | | |
| | C-625 (7) | | | | | | | | | | | |
| | Nonylphenol | | | | | | | | | | | |
| Reaction conditions | Reaction temperature (°C.) | | | | | | | | | | 60 | 60 |
| | Reaction time (Hr) | | | | | | | | | | 2.0 | 2.0 |
| NCO content in reaction solution (%) | | | | | | | | | | | 29.4 | 29.5 |

| URETHANIZING REACTION | | Example No. 12 | 13 | 14 | 15 | 16 | 17 | 18 | Comparative example No. 1 | 2 | 3 |
|---|---|---|---|---|---|---|---|---|---|---|---|
| Isocyanate component | MR-200 (1) | 500 | 500 | 500 | 500 | 500 | 500 | 250 | 500 | 500 | 500 |
| | T-80 (2) | | | | | | | 250 | | | |
| | L-5340 (3) | 4.0 | 4.0 | 4.0 | 4.0 | 4.0 | 4.0 | 4.0 | 4.0 | 4.0 | — |
| Polyol component | 1,3-butanediol | | | | | | | | | | |
| | Diethylene glycol | | | | | | | 14 | 23.8 | | |
| | PP-200 (4) | 10.5 | | | | | | | | | |
| | PEG-400 (5) | | 14.9 | | | | | | | | |
| | PP-1000 (6) | | | 19.8 | | | | | | | |
| | C-625 (7) | | | | 15.2 | | | | | | |
| | Nonylphenol | | | | | 15.6 | | | | | |
| Reaction | Reaction | 60 | 60 | 60 | 60 | 60 | 60 | — | 60 | — | |

TABLE 1-continued

| conditions | temperature (°C.) Reaction time (Hr) | 2.0 | 2.0 | 2.0 | 2.0 | 2.0 | 2.0 | — | 2.0 | — |
|---|---|---|---|---|---|---|---|---|---|---|
| NCO content in reaction solution (%) | | 29.3 | 29.4 | 29.2 | 29.0 | 29.5 | 27.9 | | 25.9 | |

| ISOCYANURATION REACTION | | No. Example No. | | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 | 13 |
| Catalyst | Ankamine K-54 (8) | 1.0 | | | | 1.0 | 1.0 | 2.0 | 1.5 | 0.5 | 0.7 | 0.7 | 0.7 | 0.7 |
| | Polycat P-41 (9) | | 0.55 | | | | | | | | | | | |
| | Potassium naphthenate | | | 0.35 | | | | | | | | | | |
| | Potassium 2-ethyhexanoate | | | | 0.2 | | | | | | 0.05 | | | |
| Cocatalyst | Triethyl phosphite | 5.0 | 2.2 | 2.5 | 2.0 | | | 3.0 | 6.0 | | 3.0 | 3.0 | 3.0 | 3.0 |
| | Tris(nonylphenyl) phosphite | | | | | 5.0 | | | | 10 | | | | |
| | Fyrol PCF (10) | | | | | | 5.0 | | | | | | | |
| | Diluent R-113 (11) | 2.0 | 1.0 | | 2.0 | 3.0 | | 3.0 | 3.0 | 4.0 | 2.0 | 2.0 | 2.0 | 2.0 |
| Reaction conditions | Reaction temperature (°C.) | 50 | 50 | 50 | 50 | 50 | 50 | 50 | 30 | 40 | 50 | 50 | 50 | 50 |
| | Reaction time (Hr) | 3.5 | 2.0 | 2.0 | 1.5 | 3.5 | 4.0 | 1.0 | 6 | 2.5 | 2.0 | 2.0 | 2.0 | 2.5 |
| Terminating reaction post treatment | Phosphoric acid | 0.5 | 0.3 | 0.3 | 0.2 | 0.5 | 0.5 | 2.0 | 0.75 | 0.25 | 0.35 | 0.35 | 0.35 | 0.35 |
| | Reaction temperature × time (°C. × Hr) | 50 × 1.0 | " | " | " | " | " | " | " | " | " | " | " | 50 × 1.0 |

| ISOCYANURATION REACTION | | No. | | | | | | | |
|---|---|---|---|---|---|---|---|---|---|
| | | Example No. | | | | | Comparative example No. | | |
| | | 14 | 15 | 16 | 17 | 18 | 1 | 2 | 3 |
| Catalyst | Ankamine K-54 (8) | 0.7 | 0.7 | 0.7 | 0.7 | 3.0 | 0.7 | 1.0 | 1.5 |
| | Polycat P-41 (9) | | | | | | | | |
| | Potassium naphthenate | | | | | | | | |
| | Potassium 2-ethyhexanoate | | | | | | | | |
| Cocatalyst | Triethyl phosphite | 3.0 | 3.0 | 3.0 | 3.0 | 3.0 | 3.0 | — | — |
| | Tris(nonylphenyl) phosphite | | | | | | | | |
| | Fyrol PCF (10) | | | | | | | | |
| | Diluent R-113 (11) | 2.0 | 2.0 | 2.0 | 2.0 | 1.0 | 2.0 | — | — |
| Reaction conditions | Reaction temperature (°C.) | 50 | 50 | 50 | 50 | 60 | 50 | 50 | 50 |
| | Reaction time (Hr) | 3.0 | 3.0 | 3.0 | 1.5 | 4.0 | 2.0 | 6.0 | 1.5 |
| Terminating reaction post treatment | Phosphoric acid | 0.35 | 1.35 | 0.35 | 0.35 | 1.5 | — | 0.5 | 0.75 |
| | Reaction temperature × time (°C. × Hr) | " | " | " | " | " | — | 50 × 1.0 | " |

Notes to Table 1
(1) Polymethylenepolyphenyl-polyisocyanate, NCO content 31.0%. Abbreviation of "Millionate MR-200" made by Nippon Polyurethane Industry Co., Ltd.
(2) Tolylene diisocyanate (Ratio of 2,4-isomer to 2,6-isomer = 80:20). Abbreviation of "Coronate T-80 (trade name) made by Nippon Polyurethane Industry Co., Ltd.
(3) A silicone surfactant. Trade name, made by U.C.C.
(4) Polyoxypropylene glycol. Molecular weight: 200. Abbreviation of Sannix PP-200 (Trade name) made by Sanyo Kasei Kogyo Co., Ltd.
(5) Polyethylene glycol. Molecular weight: 400. Trade name: PEG 400, made by Sanyo Kasei Kogyo Co., Ltd.
(6) Polyoxypropylene glycol. Molecular weight: 1000. Abbreviation of Sannix PP-1000 (Trade name) made by Sanyo Kasei Kogyo Co., Ltd.
(7) Polyesterpolyol. Hydroxyl value: 265. Trade name, made by Chardonal Co.
(8) 2,4,6-tris(dimethylaminomethyl)phenol. Trade name, made by A.C.I. Co.
(9) N,N',N''-tris(dimethylaminopropyl)hexahydro-S-triazine. Trade name, made by Sankyo Air Products Co.
(10) Tris(β-chloropropyl) phosphate. Trade name, made by Akzo Co.
(11) Trichlorotrifluoroethane. Trade name, made by Mitsui Dupont Fluorochemical K.K.

TABLE 1-1

| PRODUCT | No. Example No. | | | | | | | | | | |
|---|---|---|---|---|---|---|---|---|---|---|---|
| | 1 | 2 | 3 | 4 | 5 | 6 | 7 | 8 | 9 | 10 | 11 |
| Viscosity of reaction liquid (cP 25° C.) | 850 | 750 | 1500 | 1700 | 650 | 600 | 35000 | 3400 | 500 | 4500 | 4000 |
| NCO content (%) | 28.6 | 28.9 | 28.0 | 28.0 | 29.0 | 29.0 | 25.0 | 27.5 | 27.7 | 26.9 | 27.0 |
| Appearance | Transparent[13] | " | " | " | " | " | " | " | " | " | " |
| IR Absorption spectra | Yes[14] | " | " | " | " | " | " | " | " | " | " |
| Compatibility C-336A[12] | Transparent[15] | " | " | " | " | " | " | " | " | " | " |
| Storage stability (20° C. × 6 months) | Stable | " | " | " | " | " | " | " | " | " | " |
| Content of trimer (%) | 1.9 | 1.6 | 2.5 | 2.5 | 1.5 | 1.5 | 6.0 | 3.0 | 2.8 | 2.0 | 1.9 |

| PRODUCT | No. | | | | | | | | | |
|---|---|---|---|---|---|---|---|---|---|---|
| | Example No. | | | | | | | Comparative example No. | | |
| | 12 | 13 | 14 | 15 | 16 | 17 | 18 | 1 | 2 | 3 |
| Viscosity of reaction liquid (cP 25° C.) | 3500 | 4000 | 3700 | 3500 | 2900 | 13000 | 3500 | — | 1200 | 1800 |
| NCO content (%) | 26.8 | 27.0 | 27.0 | 26.9 | 27.3 | 26.0 | 32 | — | 28.5 | 28.5 |

TABLE 1-1-continued

| Appearance | Transparent[13] | " | " | " | " | " | " | Gelation | Lumpy[16] | " |
|---|---|---|---|---|---|---|---|---|---|---|
| IR Absorption spectra | Yes[14] | " | " | " | " | " | " | | | |
| Compatibility C-336A[12] | Transparent | " | " | " | " | " | " | | Transparent | " |
| Storage stability (20° C × 6 months) | Stable[15] | " | " | " | " | " | " | | Stable | " |
| Content of trimer (%) | 2.5 | 2.4 | 2.2 | 2.1 | 2.2 | 1.9 | 1.9 | — | 2.0 | 2.0 |

Notes to Table 1-1:
[12] Polyesterpolyol, Hydroxyl value 235, Trade name, made by Mitsui DuPont Fluorochemical K.K.
[13] Abbreviation of "Transparent brown liquid"
[14] Abbreviation of "Isocyanuration being observed"
[15] Abbreviation of "No abnormality being observed"
[16] Abbreviation of "Transparent and brown, lumpy matter being formed partially"

EXAMPLE 19

In an 1-liter four-neck flask equipped with a thermometer, a stirrer, and a nitrogen seal tube with ground glass fitting, there were placed 500 parts of MR-200 as an organic polyisocyanate, 4.0 parts of L-5340 as a surfactant, 1.0 part of FE-55 as a ferrocene compound, 1.0 part of Ankamine K-54 as a catalyst, 5.0 parts of triethyl phosphite as an organic phosphite ester, and 2.0 parts of R-113 as a diluent. The catalyst was fed as a mixture with the diluent. The air in the flask was replaced by nitrogen. The reaction mixture was stirred and heated to 50° C. After the reaction for 3.5 hours, the NCO content was measured to be 28.4 %, and the reaction liquid was found to be a transparent brown liquid. 0.5 part of phosphoric acid was added as a stopper to the reaction liquid, which was stirred at 50° C. for one hour to finish the reaction.

The resulting isocyanurate-modified-polyisocyanate was a transparent brown liquid, having an NCO content of 28.4 % and a viscosity of 900 cp/25° C., and containing a trimer as observed by infrared absorption spectra. No change was observed after 6 months. The results are shown in Table 2 and Table 2-1.

EXAMPLE 20-23

The reaction were conducted in a manner similar to that in Example 19 under the conditions shown in Table 2. The results are shown in Table 2 and Table 2-1.

EXAMPLE 24

500 parts of MR-200, 1.0 part of FE-55 as a ferrocene compound, 4.0 parts of L-5340 as a surfactant, and 6.9 parts of diethylene glycol as a polyol were placed in the same four-neck flask as in Example 19. The reaction was allowed to proceed at 60° C. for 2.0 hours. The NCO content was measured to be 29.5 %.

Subsequently, 0.7 parts of Ankamine K-54 as a catalyst, 3.0 parts of triethyl phosphite as an organic phosphite ester, and 2.0 parts of R-113 as a diluent were added thereto. The catalyst was fed as a mixture with the diluent. The reaction mixture was allowed to react at 50° C. for 2.0 hours. The NCO content was determined to be 26.8 %. To the reaction liquid, 0.35 parts of phosphoric acid was added, and the liquid was stirred at 50° C. for 1.0 hour to finish the reaction.

The resulting isocyanate-modified product was a transparent brown liquid, having an NCO content of 26.8 % and a viscosity of 4100 cp/25° C., and containing a trimer as observed by infrared absorption spectra. No change was observed after storage test for 6 months. The results are shown in Table 2 and Table 2-1.

EXAMPLES 25-28

The reactions were conducted similarly as in Example 24 under the conditions shown in Table 2. The results are shown in Table 2 and Table 2-1.

COMPARATIVE EXAMPLE 4

This Comparative example 4 was conducted in the same manner as in Example 19 except that the ferrocene compound, FE-55, was not used.
The results are shown in Table 2 and Table 2-1.

COMPARATIVE EXAMPLE 5

This Comparative example 5 was conducted in the same manner as in Example 24 except that the ferrocene compound, FE-55, was not used.
The results are shown in Table 2 and Table 2-1.

TABLE 2

| | | Example No. | | | | | | | | | | Comparative example No. | |
|---|---|---|---|---|---|---|---|---|---|---|---|---|---|
| | | 19 | 20 | 21 | 22 | 23 | 24 | 25 | 26 | 27 | 28 | 4 | 5 |
| URETHANIZING REACTION | | | | | | | | | | | | | |
| Isocyanate component | MR-200 (1) | 500 | 500 | 500 | 500 | 500 | 500 | 500 | 500 | 500 | 500 | 500 | 500 |
| | FE-55 (2) | 1.0 | 1.0 | 1.0 | 1.0 | 1.0 | 1.0 | 1.0 | 1.0 | 1.0 | 1.0 | — | — |
| | L-5340 (3) | 4.0 | 4.0 | 4.0 | 4.0 | 4.0 | 4.0 | 4.0 | 4.0 | 4.0 | 4.0 | 4.0 | 4.0 |
| Polyol component | Diethylene glycol | | | | | | 6.9 | | | | | | 6.9 |
| | PP-200 (4) | | | | | | | 10.5 | | | | | |
| | PEG-400 (5) | | | | | | | | 14.9 | | | | |
| | C-625 (6) | | | | | | | | | 15.2 | | | |
| | Nonylphenol | | | | | | | | | | 15.6 | | |
| Reaction conditions | Reaction temperature (°C.) | | | | | | 60 | 60 | 60 | 60 | 60 | | |
| | Reaction time (Hr) | | | | | | 2.0 | 2.0 | 2.0 | 2.0 | 2.0 | | |
| NCO content in | | | | | | | 29.5 | 29.3 | 29.4 | 29.0 | 29.5 | | 29.4 |

TABLE 2-continued

| | | Example No. | | | | | | | | | | Comparative example No. | |
|---|---|---|---|---|---|---|---|---|---|---|---|---|---|
| | | 19 | 20 | 21 | 22 | 23 | 24 | 25 | 26 | 27 | 28 | 4 | 5 |
| reaction solution (%) | | | | | | | | | | | | | |
| ISOCYANURATION REACTION | | | | | | | | | | | | | |
| Catalyst | Ankamine K-54 (7) | 1.0 | | 1.5 | 1.0 | 1.0 | 1.0 | 0.7 | 0.7 | 0.7 | 0.7 | 1.0 | 0.7 |
| | Polycat P-41 (8) | | 0.55 | | | | | | | | | | |
| | Diluent R-113 (9) | 2.0 | 1.0 | 3.0 | 2.0 | 2.0 | 2.0 | 2.0 | 2.0 | 2.0 | 2.0 | 2.0 | 2.0 |
| Organic phosphite ester | Triethyl phosphite | 5.0 | 2.2 | 6.0 | | | 3.0 | 3.0 | 3.0 | 3.0 | 3.0 | 5.0 | 3.0 |
| | Tri(nonylphenyl)-phosphite | | | | 5.0 | | | | | | | | |
| | PCPP (10) | | | | | 5.0 | | | | | | | |
| Reaction conditions | Reaction temperature (°C.) | 50 | 50 | 50 | 50 | 50 | 50 | 50 | 50 | 50 | 50 | 50 | 50 |
| | Reaction time (Hr) | 3.5 | 2.0 | 3.0 | 3.0 | 3.5 | 2.0 | 2.0 | 2.0 | 3.0 | 3.0 | 3.5 | 2.0 |
| Terminating reaction post treatment | Phosphoric acid Reaction temperature × time (°C. × Hr) | 0.5 50 × 1.0 | 0.3 " | 0.75 " | 0.5 " | 0.5 " | 0.35 " | 0.35 " | 0.35 " | 0.35 " | 0.35 " | 0.5 " | 0.35 " |

Notes to Table 2
(1) Polymethylenepolyphenyl-polyisocyanate. NCO content 31.0%. Abbreviation of "Millionate MR-200" made by Nippon Polyurethane Industry Co., Ltd.
(2) Ferrocene compound. Trade name. made by Ekonalick Co.
(3) Silicone surfactant. Trade name. made by U.C.C.
(4) Polyoxypropylene glycol. Molecular weight. 200. Abbreviation of Sannix PP-200 (Trade name) made by Sanyo Kasei Kogyo Co., Ltd.
(5) Polyethylene glycol. Molecular weight: 400. Trade name: PEG 400, made by Sanyo Kasei Kogyo Co., Ltd.
(6) Polyesterpolyol. Hydroxyl value. 265. Trade name. made by Shardonal Co.
(7) 2,4,6-tris(dimethylaminomethyl)phenol. Trade name. made by A.C.I. Co.
(8) N,N',N"-tris(dimethylaminopropyl)hexahydro-S-triazine. Trade name. made by Sankyo Air Products Co.
(9) Trichlorotrifluoroethane. Trade name. made by Mitsui DuPont Fluorochemical K.K.
(10) Tris(β-chloropropyl)phosphate. Trade name. Made by Akzo Co.

TABLE 2-1

| | | Example No. | | | | | | | | | Comparative example No. | |
|---|---|---|---|---|---|---|---|---|---|---|---|---|
| PRODUCT | 19 | 20 | 21 | 22 | 23 | 24 | 25 | 26 | 27 | 28 | 4 | 5 |
| Viscosity of reaction liquid (cp 25° C.) | 900 | 770 | 3650 | 700 | 660 | 4100 | 3500 | 4000 | 3600 | 3100 | 850 | 4000 |
| NCO content (%) | 28.4 | 28.9 | 27.5 | 28.9 | 29.0 | 26.8 | 26.9 | 27.0 | 26.9 | 27.5 | 28.6 | 27.0 |
| Appearance | Transparent[1] | " | " | " | " | " | " | " | " | " | " | " |
| IR Absorption spectra | Yes[2] | " | " | " | " | " | " | " | " | " | " | " |
| Storage stability (20° C. × 6 months) | Stable[3] | " | " | " | " | " | " | " | " | " | " | " |
| Content of trimer (%) | 2.1 | 1.6 | 2.0 | 1.6 | 1.5 | 2.3 | 2.1 | 2.1 | 2.1 | 1.5 | 1.9 | 2.2 |

Notes to Table 2-1
[1] Abbreviation of "Transparent brown liquid"
[2] Abbreviation of "Isocyanuration observed"
[3] Abbreviation of "No abnormality observed"

Application examples 29–45

The reaction mixtures A-liquid and B-liquid shown in Table 3, having been respectively adjusted to have a liquid temperature of 20°±1° C., were weighted out in 2-liter polyethylene beaker, and mixed for 3–5 seconds with an agitation mixer (rotation speed: 5000 rpm). The mixture was allowed to foam freely in a polyethylene bag placed in aluminum container of a size of 25×25×25 cm which had been preliminarily kept at 40° C. All of the resulting foam samples were found to have heat resistance, low smoking property, and flame retardance by the tests.

From the foams prepared as above, test specimens were prepared by cutting into a dimension of 220 mm in width and in length respectively, and 25 mm in thickness. The specimens were tested for combustion of the material according to JIS A1321 regarding a method for testing combustion of internal construction materials.

The results are shown in Table 3.

TABLE 3

| REACTION MIXTURE | Application Example No. | | | | | | | | |
|---|---|---|---|---|---|---|---|---|---|
| | 29 | 30 | 31 | 32 | 33 | 34 | 35 | 36 | 37 |
| A-LIQUID | | | | | | | | | |
| C-336A 1) | 100 | 100 | 100 | 100 | 100 | 100 | 100 | 100 | 100 |
| PP-400 2) | | | | | | | | | |
| Freon 11 | 81 | 80 | 83 | 80 | 80 | 85 | 84 | 84 | 84 |

TABLE 3-continued

| | | | | | | | | | |
|---|---|---|---|---|---|---|---|---|---|
| Perlon #9540 3) | 7.0 | 6.1 | 6.4 | 6.1 | 6.1 | 4.9 | 4.9 | 4.9 | 4.9 |
| B-LIQUID Isocyanurate-modified polymerization product | | | | | | | | | |
| Example No. | 19 | 20 | 21 | 22 | 23 | 24 | 25 | 26 | 27 |
| Parts | 310 | 304 | 320 | 304 | 303 | 329 | 327 | 326 | 327 |
| INDEX | 500 | 500 | 500 | 500 | 500 | 500 | 500 | 500 | 500 |
| TEST RESULTS | | | | | | | | | |
| Foaming rate CT (sec) | 7.0 | 7.0 | 7.5 | 6.0 | 8.0 | 5.0 | 5.5 | 6.0 | 6.0 |
| RT (sec) | 53 | 50 | 49 | 48 | 55 | 43 | 47 | 45 | 40 |
| Foam density (kg/m$^3$) | 31.0 | 32.0 | 31.0 | 31.0 | 30.0 | 29.0 | 30.0 | 29.3 | 29.5 |
| Combustion test (surface test) 4) | | | | | | | | | |
| Temperature-time area (TdA) ('C. × minutes) | 0 | 5 | 2 | 0 | 0 | 10 | 10 | 15 | 0 |
| Smoking factor (CA) | 30 | 31 | 32 | 35 | 29 | 45 | 38 | 39 | 31 |
| Flame lingering (sec) | 10 | 7 | 5 | 8 | 0 | 15 | 20 | 13 | 10 |
| Appearance | Good | Good | Good | Good | Good | Good | Good | Good | Good |

| REACTION MIXTURE | Application Example No. | | | | | | | |
|---|---|---|---|---|---|---|---|---|
| | 38 | 39 | 40 | 41 | 42 | 43 | 44 | 45 |
| A-LIQUID | | | | | | | | |
| C-336A 1) | 100 | | | 100 | 100 | 100 | 100 | 100 |
| PP-400 2) | | 100 | 100 | | | | | |
| Freon 11 | 83 | 93 | 98 | 58 | 110 | 86 | 84 | 76 |
| Perlon #9540 3) | 4.8 | 11.1 | 7.8 | 2.8 | 9.3 | 6.2 | 4.9 | 5.1 |
| B-LIQUID Isocyanurate-modified polymerization product | | | | | | | | |
| Example No. | 28 | 19 | 24 | 19 | 19 | Comparative example 4 | Comparative example 5 | MR-200 |
| Parts | 320 | 370 | 392 | 186 | 465 | 308 | 326 | 284 |
| INDEX | 500 | 500 | 500 | 300 | 750 | 500 | 500 | 500 |
| TEST RESULTS | | | | | | | | |
| Foaming rate CT (sec) | 5.5 | 8.0 | 7.0 | 6.0 | 7.0 | 7.2 | 6.3 | 5.0 |
| RT (sec) | 42 | 57 | 49 | 60 | 42 | 51 | 45 | 49 |
| Foam density (kg/m$^3$) | 29.0 | 30.5 | 29.0 | 28.0 | 33.0 | 31.0 | 31.5 | 32.5 |
| Combustion test (surface test) 4) | | | | | | | | |
| Temperature-time area (TdA) ('C. × minutes) | 20 | 35 | 40 | 0 | 0 | 10 | 35 | 70 |
| Smoking factor (CA) | 39 | 43 | 50 | 27 | 37 | 40 | 47 | 55 |
| Flame lingering (sec) | 21 | 31 | 40 | 5 | 0 | 30 | 60 | 75 |
| Appearance | Good | Good | Good | Good | Good | Crack[5] | Crack[6] | Crack[7] |

Notes to Table 3
1) Polyesterpolyol. Hydroxyl value 235. Trade name, made by Chardonal Co.
2) Polyoxypropylene glycol. Molecular weight 400. Abbreviation of Sannix PP-400, made by Sanyo Kasei Kogyo Co., Ltd.
3) Fatty acid metal salt catalyst. Trade name, made by Chardonal Co.
4) Tested according to JIS A1321
5) Abbreviation of "crack occurring"
6) Abbreviation of "considerable crack occurring"
7) Abbreviation of "penetrating crack occurring"
In Tables 3 and 5-1, "CT" means cream time, and "RT" means rise time.

EXAMPLE 46

(Preparation of Modified Polymethylenepolyphenyle-Polyisocyanate)

In an 1-liter four-neck flask equipped with a thermometer, a stirrer, and a nitrogen seal tube with ground glass fitting, there were placed 500 parts of MR-200 as a polymeric MDI, 1.0 part of Ankamine K-54 as a trimeriztion catalyst, and 2.0 parts of R-113 as a diluent in a mixture. Further, 5.0 parts of triethyl phosphite was added thereto as an organic phosphite ester compound. The air in the flask was replaced by nitrogen. The isocyanuration reaction was carried out with stirring at 50° C. for 4 hours. Subsequently, 0.4 part of phosphoric acid was added, and stirred at 50° C. for one hour to finish the reaction.

The resulting product was a transparent brown liquid in appearance, having an NCO content of 28.7 %, a viscosity of 950 cp/25° C., and a trimer content of 1.8 %.

EXAMPLES 47-50

Modified products were prepared from the polymethylenepolyphenyl-polyisocyanate, the catalyst, the organic phosphite ester compound and the diluent as shown in Table 4 by using the same reactor as in Example 46 in the same manner as in Example 46, under the conditions shown in Table 4-1. The NCO content, the viscosity, and the trimer, etc. are shown in Table 4-1.

EXAMPLE 51

(Preparation of Partially Urethanized Modified Polymethylenepolyphenyl-polyisocyanate)

In an 1-liter four-neck flask equipped with a thermometer, a stirrer, and a nitrogen seal tube with ground glass fitting, there were placed 500 parts of MR-200 as a polymethylenepolyphenyl-polyisocyanate, 6.9 parts of diethylene glycol as a polyol. The air in the flask was replaced by nitrogen, and the urethanizing reaction was carried out with stirring at 60° C. for 2 hours. The NCO content after the reaction was 29.4 %.

Subsequently, 0.8 part of Ankamine K-54 as a trimerization catalyst mixed with R-113 as a diluent, and 4.0 parts of triethyl phosphite as an organic phosphite ester were added, and the isocyanuration reaction was carried out with stirring at 50° C. for 1.5 hours. Then 0.4 part of phosphoric acid was added and stirred at 50° C. for 1.5 hours to finish the reaction.

The resulting product was a transparent brown liquid in appearance, having an NCO content of 27.0 %, a viscosity of 4000 cp/25° C., and a trimer content of 2.4 %.

EXAMPLES 52–54

Modified products were prepared by reacting a polymethylenepolyphenyl-polyisocyanate with a polyol in a ratio as shown in Table 4 in the same reactor as in Example 46 under the conditions shown in Table 4-1, further adding the catalyst etc. as shown in Table 4-1, and conducting reaction under the conditions in Table 4-1. The NCO contents etc. are shown in Table 4-1.

TABLE 4

| | No. Example No. | | | | | | | | |
|---|---|---|---|---|---|---|---|---|---|
| | 46 | 47 | 48 | 49 | 50 | 51 | 52 | 53 | 54 |
| URETHANIZING REACTION | | | | | | | | | |
| A-component MR-200 1) | 500 | 500 | 500 | 500 | 500 | 500 | 500 | 500 | 500 |
| B-component | | | | | | | | | |
| Diethylene glycol | | | | | | 6.9 | | | |
| PP-200 2) | | | | | | | 10.5 | | |
| PEG-200 3) | | | | | | | | 10.5 | |
| Nonylphenol | | | | | | | | | 15.6 |
| Reaction conditions | | | | | | | | | |
| Reaction temperature (°C.) | | | | | | 60 | 60 | 60 | 60 |
| Reaction time (Hr) | | | | | | 2 | 2 | 2 | 2 |
| NCO content of reaction liquid (%) | | | | | | 29.4 | 29.4 | 29.4 | 29.4 |
| ISOCYANURATION REACTION | | | | | | | | | |
| Catalyst | | | | | | | | | |
| Ankamine K-54 4) | 1.0 | | | 1.5 | 1.5 | 0.8 | 0.8 | 0.8 | 0.8 |
| Polycat P-41 5) | | 0.55 | | | | | | | |
| Potassium naphthanate | | | 0.35 | | | | | | |
| Phosphite ester | | | | | | | | | |
| Triethyl phosphite | 5.0 | 2.75 | | 5.0 | 3.0 | 4.0 | 4.0 | 4.0 | 4.0 |
| TCPP 6) | | | 1.4 | | | | | | |
| Diluent R-113 7) | 2.0 | 1.0 | | 3.0 | 3.0 | 2.5 | 2.5 | 2.5 | 2.5 |

Notes to Table 4
1) Polymethylenepolyphenyl-polyisocyanate, NCO content: 31.0%, Abbreviation of "Millionate MR-200", made by Nippon Polyurethane Industry Co., Ltd
2) Polyoxypropylene glycol, Molecular weight: 200, Abbreviation of Sannix PP-200 (Trade name) made by Sanyo Kasei Kogyo Co., Ltd.
3) Polyethylene glycol, Molecular weight: 200, Trade name, made by Sanyo Kasei Kogyo Co., Ltd.
4) 2,4,6-tris(dimethylaminomethyl)phenol, Trade name, made by A.C.I Co
5) N,N',N''-tris(dimethylaminopropyl)hexahydro-S-triazine, Trade name, made by Sankyo Air Products Co.
6) Tris(β-chloropropyl)phosphate, Trade name, made by Akzo Co.
7) Trichlortrifluoroethane, Trade name, made by Mitsui DuPont Fluorochemical K.K.
8) Abbreviation of "Organic phosphite ester compound"

TABLE 4-1

| | No. Example No. | | | | |
|---|---|---|---|---|---|
| | 46 | 47 | 48 | 49 | 50 |
| ISOCYANURATION REACTION | | | | | |
| Reaction conditions | | | | | |
| Reaction temperature (°C.) | 50 | 50 | 50 | 50 | 50 |
| Reaction time (Hr) | 4.0 | 2.0 | 2.5 | 2.0 | 2.0 |
| Post-treatment with stopper | | | | | |
| Phosphoric acid | 0.4 | 0.2 | 0.4 | 0.6 | 0.6 |
| Reaction temperature × time (°C. × Hr) | 50 × 1.0 | 50 × 1.0 | 50 × 1.0 | 50 × 1.0 | 50 × 1.0 |
| PRODUCT | | | | | |
| Viscosity of product liquid (cp/25° C.) | 950 | 1500 | 2000 | 3400 | 11000 |
| NCO content (%) | 28.7 | 28.6 | 28.6 | 27.6 | 26.5 |
| External appearance | Transparent brown liquid | Transparent brown liquid | Transparent brown liquid | Transparent brown liquid | Transparent brown liquid |
| Trimer content (%) | 1.8 | 1.9 | 1.9 | 2.9 | 4.0 |

| | No. Example No. | | | |
|---|---|---|---|---|
| | 51 | 52 | 53 | 54 |
| ISOCYANURATION REACTION | | | | |
| Reaction conditions | | | | |
| Reaction temperature (°C.) | 50 | 50 | 50 | 50 |

| TABLE 4-1-continued | | | | |
|---|---|---|---|---|
| Reaction time (Hr) | 1.5 | 2.0 | 2.0 | 2.0 |
| Post-treatment with stopper | | | | |
| Phosphoric acid | 0.3 | 0.3 | 0.3 | 0.3 |
| Reaction temperature × time (°C × Hr) | 50 × 1.0 | 50 × 1.0 | 50 × 1.0 | 50 × 1.0 |
| PRODUCT | | | | |
| Viscosity of product liquid (cp/25° C.) | 4000 | 3500 | 3700 | 2900 |
| NCO content (%) | 27.0 | 26.8 | 26.9 | 27.3 |
| External appearance | Transparent brown liquid | Transparent brown liquid | Transparent brown liquid | Transparent brown liquid |
| Trimer content (%) | 2.4 | 2.5 | 2.6 | 2.1 |

EXAMPLES 55–68 AND COMPARATIVE EXAMPLE 6

(Preparation of Foams and Test for Properties)

The A-liquid and the B-liquid for the reaction mixture shown in Table 5, having been respectively adjusted to have a liquid temperature of 20°±1° C., were weighted out in 2-liter polyethylene beaker, and mixed for 3–5 seconds with an agitation mixer (rotation speed: 5000 rpm). The mixture was allowed to foam freely in a polyethylene bag placed in aluminum container of a size of 25×25×25 cm which had been preliminarily kept at 40° C. All of the resulting foam samples were found to have heat resistance, low smoking property, and flame retardance by the tests. The results are shown in Table 5-1.

TABLE 5

| REACTION MIXING LIQUID | No. Example No. | | | | | | | |
|---|---|---|---|---|---|---|---|---|
| | 55 | 56 | 57 | 58 | 59 | 60 | 61 | 62 |
| A-LIQUID | | | | | | | | |
| PP-400 1) | 100 | | | | | | | |
| PP-1000 2) | | 100 | | | | | | |
| PEG-400 3) | | | 100 | | | | | |
| C-336A 4) | | | | 100 | | 100 | 100 | 100 |
| App315 5) | | | | | 100 | | | |
| 452SA 6) | | | | | | | | |
| Freon 11 | 92 | 63 | 92 | 80 | 101 | | | |
| Catalyst | | | | | | | | |
| Potassium 2-ethylhexanoate 7) | 7.3 | 3.4 | 7.0 | 8.1 | 8.2 | 5.5 | 5.5 | 5.6 |
| Dimethylaminopropionic acid 8) | | 1.0 | | | | 2.7 | 2.7 | 2.8 |
| Polycat P-42 9) | | | | | | 2.0 | | |
| B-LIQUID | | | | | | | | |
| Isocyanurate-modified product | | | | | | | | |
| Example No. | 46 | 46 | 46 | 46 | 46 | 47 | 48 | 49 |
| Parts | | | | | | | | |
| MR-200 10) | 366 | 220 | 366 | 306 | 410 | 308 | 308 | 319 |
| L-5340 11) | 3.7 | 2.6 | 3.7 | 3.2 | 4.1 | 3.3 | 3.3 | 3.4 |

| REACTION MIXING LIQUID | No. Example No. | | | | | | Comparative example No. 6 |
|---|---|---|---|---|---|---|---|
| | 63 | 64 | 65 | 66 | 67 | 68 | |
| A-LIQUID | | | | | | | |
| PP-400 1) | | | | | | | |
| PP-1000 2) | | | | | | | |
| PEG-400 3) | | | | | | | |
| C-336A 4) | 100 | 100 | 100 | 100 | 100 | | 100 |
| App315 5) | | | | | | | |
| 452SA 6) | | | | | | 100 | |
| Freon 11 | | | | | | 136 | |
| Catalyst | | | | | | | |
| Potassium 2-ethylhexanoate 7) | 5.8 | 4.3 | 4.3 | 4.3 | 4.0 | 5.9 | 4.2 |
| Dimethylaminopropionic acid 8) | 2.8 | 2.1 | 2.1 | 2.1 | 2.0 | | |
| Polycat P-42 9) | | | | | | 5.9 | |
| B-LIQUID | | | | | | | |
| Isocyanurate-modified product | | | | | | | |
| Example No. | 50 | 51 | 52 | 53 | 54 | 46 | |
| Parts | | | 328 | 327 | 322 | 587 | |
| MR-200 10) | 332 | 326 | | | | | 279 |

TABLE 5-continued

| L5340 11) | 3.5 | 3.4 | 3.4 | 3.4 | 3.4 | | 3.0 |

Notes to Table 5

1) Polyoxypropylene glycol. Molecular weight, 400. Abbreviation of "Sannix PP-400", made by Sanyo Kasei Kogyo Co., Ltd
2) Polyoxypropylene glycol. Molecular weight 1000. Abbreviation of "Sannix PP-1000", made by Sanyo Kasei Kogyo Co., Ltd.
3) Polyethylene glycol. Molecular weight, 400. Trade name. made by Sanyo Kasei Kogyo Co., Ltd
4) Polyesterpolyol. Hydroxyl value 235. Trade name. Made by Chardonal Co
5) Polyesterpolyol. Hydroxyl value 315. Trade name. Made by U.C.C
6) Sucrose type amine polyol. Hydroxyl value 450. Trade name, made by Asahi Glass Co., Ltd
7) Abbreviation of "potassium 2-ethylhexanate containing PP-400 as a content of 50%"
8) Abbreviation of "potassium dimethylaminopropionate containing diethylene glycol as a content of 50%"
9) Trade name, made by Sankyo Air Products K.K
10) Polymethylenepolyphenyl polyisocyanate. NCO content: 31.0%. Abbreviation of "Millionate MR-200", made by Nippon Polyurethane K.K.
11) Silicone surfactant. Trade name. made by U.C.C.

Test for Combustion of Internal Construction Material According to JIS A1321:

The foam prepared in Example was cut into a specimen of 220 mm in length, 220 mm in width, and 25 mm in thickness. The specimen is heated in a heating furnace by combinedly employing an electric heater as the main heat source and propane gas as a auxiliary heat source for the defined time length. Occurrence of crack or deformation and the level thereof, time of lingering flame after the stop of the heating, the exhaust gas temperature curve are measured. The same measurement is conducted with a perlite plate as the comparison standard. From the difference of the curves, the heating value (temperature-time area: TdA °C.×min.), the smoking factor ($C_A$) are measured, and the combustibility of the material is evaluated according to a pierced hole test and a surface test.

Heat Resistance Test

Test specimen is cut into a cube having a width, a length, and a thickness of approximately 6 cm, and is tested according to JIS A9514.

Adhesiveness Test

By use of a sandwich panel prepared in Examples, the peeling adhesiveness between the panel plate and the foam is measured.

TABLE 5-1

| PROPERTIES | Example No. 55 | 56 | 57 | 58 | 59 | 60 | 61 | 62 | 63 | 64 |
|---|---|---|---|---|---|---|---|---|---|---|
| Index (%) | 500 | 750 | 500 | 500 | 500 | 500 | 500 | 500 | 500 | 500 |
| Foaming rate | | | | | | | | | | |
| CT(sec) | 7.5 | 8.0 | 6.0 | 6.5 | 8.0 | 7.0 | 7.0 | 6.5 | 5.0 | 5.5 |
| RT(sec) | 59 | 50 | 49 | 52 | 55 | 54 | 55 | 55 | 43 | 48 |
| Foam density (kg/m³) | 30.0 | 29.9 | 31.0 | 30.5 | 32.0 | 34.0 | 34.0 | 32.0 | 33.0 | 31.0 |
| Compression strength | | | | | | | | | | |
| Full-time 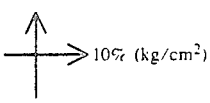 10% (kg/cm²) | 0.8 | 0.4 | 0.7 | 0.75 | 0.85 | 0.8 | 0.6 | 0.75 | 0.65 | 0.7 |
| 300° C. × 30′ 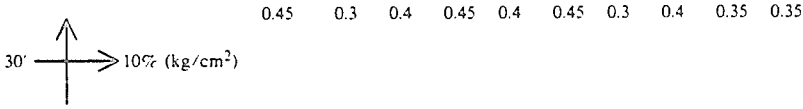 10% (kg/cm²) | 0.45 | 0.3 | 0.4 | 0.45 | 0.4 | 0.45 | 0.3 | 0.4 | 0.35 | 0.35 |
| External appearance | Good | " | " | " | " | " | " | " | " | " |
| Adhesiveness | Good | " | " | " | " | " | " | " | " | " |
| Oxygen index | 26.0 | 25.0 | 26.5 | 26.5 | 26.7 | 25.5 | 25.0 | 26.5 | 26.0 | 26.0 |
| Surface test 1) | | | | | | | | | | |
| Temperature time area (TdA) (°C. × minutes) | 41 | 63 | 42 | 11 | 10 | 1 | 10 | 21 | 0 | 23 |
| Smoking factor | 50 | 55 | 51 | 32 | 34 | 35 | 36 | 37 | 38 | 38 |
| Flame lingering (sec) | 31 | 45 | 30 | 10 | 10 | 10 | 10 | 0 | 15 | 7 |
| Appearance | Good | " | " | " | " | " | " | " | " | " |

| PROPERTIES | Application Example No. 65 | 66 | 67 | 68 | Comparative example No. 6 |
|---|---|---|---|---|---|
| Index (%) | 500 | 500 | 500 | 500 | 500 |
| Foaming rate | | | | | |
| CT (sec) | 6.0 | 5.8 | 6.0 | 7.9 | 7.0 |
| RT (sec) | 50 | 45 | 50 | 49 | 47 |
| Foam density (kg/m³) | 32.0 | 30.0 | 31.5 | 32.0 | 33.0 |
| Compression strength | | | | | |
| Full-time 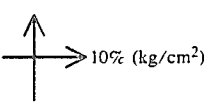 10% (kg/cm²) | 0.7 | 0.7 | 0.7 | 0.85 | 0.83 |

TABLE 5-1-continued

| | | | | | |
|---|---|---|---|---|---|
| 300° C. × 30' → 10% (kg/cm²) | 0.35 | 0.35 | 0.35 | 0.45 | 0.3 |
| External appearance | Good | Good | Good | Good | Crack 2) |
| Adhesiveness | Good | Good | Good | Good | No 3) |
| Oxygen index | 26.0 | 26.0 | 26.0 | 26.8 | 25.5 |
| Surface test 1) | | | | | |
| Temperature time area (TdA) (°C. × minutes) | 25 | 20 | 25 | 35 | 52 |
| Smoking factor | 38 | 38 | 37 | 49 | 50 |
| Flame lingering (sec) | 9 | 13 | 15 | 10 | 27 |
| Appearance | Good | Good | Good | Good | Crack 4) |

Notes to Table 5-1:
1) Tested according to JIS K7201
2) Abbreviation of "Crack occuring"
3) Abbreviation of "Slightly inferior"
4) Abbreviation of "Crack and distortion occuring"

EXAMPLES 69-77 AND COMPARATIVE EXAMPLE 7

The A-liquid and the B-liquid for the reaction mixture shown in Table 6, having been respectively adjusted to have a liquid temperature of 20°±1° C., were weighted out in a 2-liter polyethylene beaker, and mixed for 3-5 seconds with an agitation mixer (rotation speed: 5000 rpm). The mixture was poured into an aluminum mold having width, length, and depth of 46×46×25 mm with a face material of a color steel plate of 0.27 mm thick placed on the bottom, which has been previously allowed to warm to 50° C. Immediately, another face material of color steel plate of 0.27 mm thick was set on the foam, and the cover of the mold was closed to press the foam which was kept at 50° C. for 30 minutes to cure the foam. Thereafter the product was released from the mold to give a sandwich panel. The results of the measurement of the properties are shown in Table 6.

TABLE 6

| REACTION MIXING LIQUID | 69 | 70 | 71 | 72 | 73 | 74 | 75 | 76 | 77 | Comparative example No. 7 |
|---|---|---|---|---|---|---|---|---|---|---|
| A-LIQUID | | | | | | | | | | |
| PP-200 1) | 20 | 20 | 20 | 20 | 20 | 20 | 20 | 20 | 20 | 20 |
| C-336A 2) | 70 | 70 | 70 | 70 | 70 | 70 | 70 | 70 | 70 | 70 |
| 452SA 3) | 10 | 10 | 10 | 10 | 10 | 10 | 10 | 10 | 10 | 10 |
| Freon 11 | 107 | 107 | 107 | 110 | 113 | 112 | 112 | 112 | 111 | 98.7 |
| Catalyst | | | | | | | | | | |
| Potassium 2-ethylhexanoate 4) | 6.3 | 6.3 | 6.3 | 6.5 | 6.8 | 6.0 | 6.5 | 6.6 | 6.8 | 4.3 |
| Polycat P-42 5) | 2.1 | 2.1 | 2.1 | 2.2 | 2.3 | 2.0 | 2.1 | 1.9 | 1.9 | 1.4 |
| B-LIQUID | | | | | | | | | | |
| Isocyanurate-modified product | | | | | | | | | | |
| Example No. | 46 | 47 | 48 | 49 | 50 | 51 | 52 | 53 | 54 | — |
| Parts | 420 | 421 | 421 | 436 | 454 | 446 | 449 | 448 | 441 | — |
| MR-200 6) | | | | | | | | | | 382 |
| L-5340 7) | 4.2 | 4.2 | 4.2 | 4.3 | 4.4 | 4.4 | 4.4 | 4.4 | 4.3 | 3.9 |
| PROPERTIES | | | | | | | | | | |
| Index (%) | 500 | 500 | 500 | 500 | 500 | 500 | 500 | 500 | 500 | 500 |
| Foam density (kg/m³) | 30.5 | 32.0 | 31.0 | 31.5 | 30.5 | 29.5 | 30.0 | 29.0 | 31.4 | 32.5 |
| Pierced hole test | | | | | | | | | | |
| Temperature time area (TdA) (°C. × minutes) | 0 | 0 | 0 | 0 | 0 | 0 | 0 | 0 | 0 | 0 |
| Smoking factor | 34 | 37 | 38 | 33 | 41 | 39 | 37 | 32 | 35 | 57 |
| Foam weight retention rate (%) | 78 | 71 | 73 | 74 | 70 | 73 | 72 | 74 | 74 | 60 |
| Appearance | Good | Good | Good | Good | Good | Good | Good | Good | Good | Crack 9) |

Notes to Table 6:
1) Polyoxypropylene glycol, Molecular weight: 200, Abbreviation of "Sannix PP-100", made by Sanyo Kasei Kogyo Co., Ltd.
2) Polyesterpolyol, Hydroxyl value: 235, Trade name, made by Chardonal Co.
3) Sucrose type amine polyol, Hydroxyl value: 450, Trade name, made by Asahi Glass Co., Ltd.
4) Abbreviation of "potassium 2-ethylhexanate containing polyoxypropylene glycol (molecular weight: 400) as a content of 50%"
5) Trade name, made by Sankyo Air Products K.K
6) Polymethylenepolyphenyl polyisocyanate, NCO content: 31.0%, Abbreviation of "Millionate MR-200", made by Nippon Polyurethane Industry Co., Ltd.
7) Silicone surfactant, Trade name, made by U.C.C.
8) Measured according to JIS K-7201
9) Abbreviation of "crack and deformation occured:

I claim:

1. A modified organic polyisocyanate which contains an isocyanurate ring, produced from the reaction of an original polyisocyanate selected from the group consisting of organic polyisocyanates, partially urethanized organic polyisocyanates, and mixtures thereof, in a reaction mixture comprising a trimerization catalyst, an organic phosphite ester, and a surfactant, to cause isocyanuration of not more than about 20% by weight of the isocyanate groups in the original polyisocyanate.

2. The modified polyisocyanate of claim 1, wherein the partially urethanized organic polyisocyanate is prepared from the reaction of from about 1% to about 10% by weight of the isocyanate groups of an organic polyisocyanate with a hydroxyl-group-containing compound having a molecular weight of not more than about 2000.

3. The modified polyisocyanate of claim 2 wherein the hydroxyl-group-containing compound has a molecular weight of not more than about 1000 and has a functionality of not more than three.

4. The modified polyisocyanate of claim 2 wherein the urethanizing reaction of the organic polyisocyanate and the hydroxyl-group-containing compound is conducted at a temperature of from about 60° C. to about 90° C.

5. The modified polyisocyanate of claim 4 wherein the urethanizing reaction of the organic polyisocyanate and the hydroxyl-group-containing compound is conducted at a temperature of from about 60° C. to about 90° C.

6. The modified polyisocyanate of claim 3 wherein the hydroxyl-group-containing compound is selected from the group consisting of primary alcohols, diols, triols, polyester polyols, polyether polyols, and mixtures thereof.

7. The modified polyisocyanate of claim 6 wherein the primary alcohol is of the formula R'OH, wherein R' is selected from the group consisting of alkyl, arylalkyl, alkylaryl, aryl, and alkenyl.

8. The modified polyisocyanate of claim 7 wherein the primary alcohol is selected from the group consisting of 2-ethylhexyl alcohol, lauryl alcohol, and nonyl alcohol.

9. The modified polyisocyanate of claim 16 wherein the diol is selected from the group consisting of ethylene glycol, diethylene glycol, 1,3-butanediol, 1,4-butanediol, propylene glycol, dipropylene glycol, neopentyl glycol, 1,6-hexane glycol, 2-ethylhexanediol, 2,2,4-trimethylpentanediol, polyester diols, and polyether diols.

10. The modified polyisocyanate of claim 6 wherein the triol is selected from the group consisting of trimethylolethane, trimethylolpropane, and glycerin.

11. The modified polyisocyanate of claim 1 wherein the organic polyisocyanate is selected from the group consisting of 2,4- or 4,4'-diisocyanatodiphenyl ether, 2,4- or 2,6-toluene diisocyanate, 4,6-dimethyl-1,3-phenylene diisocyanate, 4,4'-diisocyanatodibenzyl, 9,10-anthracene diisocyanate, 3,3'-dimethyl-4,4'-diisocyanatodiphenylmethane, 2,6'-dimethyl-4,4'-diisocyanatodiphenyl, xylylene diisocyanate, and 2,4'- or 4,4'-diphenylmethane diisocyanate.

12. The modified polyisocyanate of claim 1 wherein the organic polyisocyanate is an aromatic polyisocyanate.

13. The modified polyisocyanate of claim 12 wherein the organic polyisocyanate is a polymethylenepolyphenyl polyisocyanate.

14. The modified polyisocyanate of claim 13 wherein the polymethylenepolyphenyl polyisocyanate is of the formula

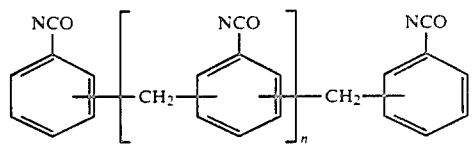

wherein n is a whole number having a value of from 0 to 8 inclusive.

15. The modified polyisocyanate of claim 2, wherein the partially urethanized organic polyisocyanate is the reaction product of a polymethylenepolyphenyl polyisocyanate with a polyol having a molecular weight of from about 62 to about 1000.

16. The modified polyisocyanate of claim 1 wherein the trimerization catalyst is selected from the group consisting of alkali metal salts, tertiary amines, and mixtures thereof.

17. The modified polyisocyanate of claim 16 wherein the alkali metal salt is selected from the group consisting of phenolates, alcoholates, and salts of carboxylic acids having from 2 to 12 carbons.

18. The modified polyisocyanate of claim 17 wherein the alkali metal salt is potassium phenolate or sodium methoxide.

19. The modified polyisocyanate of claim 16 wherein the tertiary amine is selected from the group consisting of 2,4,6-tris(dimethylamino-methyl)phenol, 2,4-bis(dimethylaminomethyl)phenol, 2,6-di-tertiary-butyl-4-dimethylaminotrimethylsilanephenol, triethylamine, N,N',N''-tris(dimethylaminopropyl)hexahydrotriazine, and diazabicycloundecene.

20. The modified polyisocyanate of claim 1 wherein the trimerization catalyst is present in the reaction mixture in an amount ranging from about 0.005% to about 0.5% by weight of the amount of the original polyisocyanate.

21. The modified polyisocyanate of claim 20 wherein the catalyst is mixed with a diluent before being added to the reaction mixture.

22. The modified polyisocyanate of claim 21 wherein the diluent is on combustible and is inactive to isocyanate.

23. The modified polyisocyanate of claim 22 wherein the diluent is selected from the group consisting of methylene chloride, trichlorofluoromethane, dichlorodifluoromethane, dichlorotetrafluoroethane, and trichlorotrifluoroethane.

24. The modified polyisocyanate of claim 1 wherein the organic phosphite ester is a diester of the formula (RO)$_2$P(O)H, wherein R is selected from the group consisting of alkyl having from 1 to 20 carbons, aryl, and combinations thereof.

25. The modified polyisocyanate of claim 24 wherein R is a phenyl group which may be substituted with an alkyl of from 1 to 20 carbons.

26. The modified polyisocyanate of claim 24 wherein the diester is dilauryl hydrogen phosphite or diphenyl hydrogen phosphite.

27. The modified polyisocyanate of claim 24 wherein R is an alkyl group which may be partially substituted by a halogen.

28. The modified polyisocyanate of claim 27 wherein the diester is tris(2,3-dichloropropyl) phosphite.

29. The modified polyisocyanate of claim 24 wherein the oxygen atom in the phosphite is substituted by a sulfur atom.

30. The modified polyisocyanate of claim 29 wherein the diester is trilauryl trithiophosphate.

31. The modified polyisocyanate of claim 1 wherein the organic phosphite ester is a triester of the formula (R—O—)$_3$P, wherein R is selected from the group consisting of alkyl having from 1 to 20 carbons, aryl, and combinations thereof.

32. The modified polyisocyanate of claim 31 wherein R is a phenyl group which may be substituted with an alkyl of from 1 to 20 carbons.

33. The modified polyisocyanate of claim 31 wherein the triester is selected from the group consisting of triethyl phosphite, tributyl phosphite, tris(2-ethylhexyl) phosphite, tridecyl phosphite, trilauryl phosphite, tris(tridecyl) phosphite, tristearyl phosphite, triphenyl phosphite, tris(nonylphenyl) phosphite, and tris(2,4-di-t-butylphenyl) phosphite.

34. The modified polyisocyanate of claim 31 wherein R is an alkyl group which may be partially substituted by a halogen.

35. The modified polyisocyanate of claim 34 wherein the triester is tris($\beta$-chloropropyl) phosphate.

36. The modified polyisocyanate of claim 1 wherein the organic phosphite ester is selected from the group consisting of di-, tri-, and tetra-phosphites derived from polyhydric alcohols, diphosphites derived from bisphenol series compounds, and polyphosphites.

37. The modified polyisocyanate of claim 36 wherein the di-, tri-, and tetra-phosphites derived from polyhydric alcohols are selected from the group consisting of distearyl pentraerythrityl diphosphite, ditridecyl pentaerythritol diphosphite, dinonylphenyl pentaerythritol diphosphite, tetraphenyl tetratridecyl pentaerythritol tetraphosphite, tetraphenyl dipropylene glycol diphosphite, and tripentaerythritol trisphosphite.

38. The modified polyisocyanate of claim 36 wherein the diphosphites derived from bisphenol series compounds are selected from the group consisting of 4,4'-butylidene-bis(3-methyl-6,6-butylphenyl-ditridecyl) phosphite and dialkyl bisphenol A disphosphite, wherein the dialkyl group contains from 1 to 20 carbons.

39. The modified polyisocyanate of claim 36 wherein the polyphosphite is a hydrogenated bisphenol A phosphite polymer having a molecular weight of from about 2400 to about 3000.

40. The modified polyisocynate of claim 1 wherein the organic phosphite ester is present in the reaction mixture in an amount, by weight, of from about 1/10 to about 20 times the amount of the catalyst.

41. The modified polyisocyanate of claim 1 wherein the surfactant is added to the reaction mixture either in the initial stage or in a later stage of the isocyanuration reaction.

42. The modified polyisocyanate of claim 1 wherein the surfactant is prepared from the reaction of a polyglycol ether with an organic compound having one reactive hydrogen atom.

43. The modified polyisocyanate of claim 42 wherein the organic compound having one reactive hydrogen atom is selected from the group consisting of alcohols, phenols, phenol compounds having one or more alkyl substituents, thiols, primary and secondary amines, carboxylic acids, sulfonic acids, and amides of carboxylic and sulfonic acids.

44. The modified polyisocyanate of claim 42 wherein the polyglycol ether is prepared from the reaction of an alkylene oxide with polyethylene glycol or polypropylene glycol.

45. The modified polyisocyanate of claim 44 wherein the alkylene oxide is selected from the group consisting of ethylene oxide, propylene oxide, and butylene oxide.

46. The modified polyisocyanate of claim 44 wherein the alkylene oxide is ethylene oxide.

47. The modified polyisocyanate of claim 1 wherein the surfactant is a polyethylene glycol ether.

48. The modified polyisocyanate of claim 43 wherein the surfactant is polyethylene glycol nonylphenyl ether.

49. The modified polyisocyanate of claim 1 wherein the surfactant is prepared by first polymerizing a 1,2-alkylene oxide or a substituted alkylene oxide in the presence of an alkali catalyst to give a corresponding water-insoluble polyalkylene glycol, and by subsequently condensing the polyalkylene glycol with ethylene oxide.

50. The modified polyisocyanate of claim 49 wherein the 1,2-alkylene oxide or the substituted alkylene oxide is selected from the group consisting of butylene oxide, amylene oxide, phenylethylene oxide, cyclohexene oxide, propylene oxide, and mixtures thereof.

51. The modified polyisocyanate of claim 1 wherein the surfactant is prepared by first forming an aldehyde from the catalytic reaction of a polyolefin with carbon monoxide and hydrogen, by reducing the resulting aldehyde into an alcohol, and by subsequently reacting the alcohol with ethylene oxide.

52. The modified polyisocyanate of claim 51 wherein the polyolefin is selected from the group consisting of tripropylene, tetrapropylene, pentapropylene, diisobutylene, triisobutylene, tetrabutylene, propylene-isobutylene, and tributene.

53. The modified polyisocyanate of claim 51 wherein the surfactant is a polyoxyethylene alkyl ether.

54. The modified polyisocyanate of claim 53 wherein the surfactant is polyoxyethylene lauryl ether or polyoxyethylene oleyl ether.

55. The modified polyisocyanate of claim 1 wherein the surfactant is of the formula $$R'Si \begin{cases} O(RSiO)_p(C_nH_{2n}O)_zR'' \\ O(RSiO)_q(C_nH_{2n}O)_zR'' \\ O(RSiO)_r(C_nH_{2n}O)_zR'' \end{cases}$$

wherein R, R', and R'' are alkyl groups having from 1 to 20 carbons; wherein p, q, and r are whole numbers having values of 1 or greater; wherein n is a whole number having a value of from 2 to 4 inclusive; and wherein z is a whole number having a value of 5 or greater.

56. The modified polyisocyanate of claim 1 wherein the surfactant is present in an amount ranging from about 0.1% to about 2% by weight of the amount of the original polyisocyanate.

57. The modified polyisocyanate of claim 1 wherein the reaction mixture further comprises a ferrocene compound.

58. The modified polyisocyanate of claim 57 wherein the ferrocene compound is of the formula

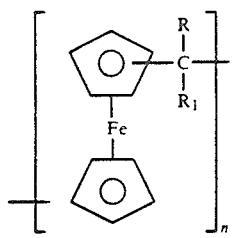

wherein R and $R_1$ are selected from the group consisting of hydrogen, alkyl, alkenyl, arylalkyl, aryl, and combinations thereof; wherein R and $R_1$, together with the carbon atom mutually attached thereto, are capable of forming a ring; wherein n is a whole number having a value of 1 or greater; and wherein the position of the substitution in the ferrocene nucleus is 1,2-, 1,3-, 1,1'-, or a mixture thereof.

59. The modified polyisocyanate of claim 58 wherein the ferrocene compound is a mono- or di-lower alkyl ($C_{1-8}$) dicyclopentadienyl iron compound, or a dimer or polymeric product of the reaction of an aldehyde or a ketone with dicyclopentadienyl iron or a dicyclopentadienyl iron derivative wherein the substituent is an alkyl group containing from 1 to 8 carbon atoms.

60. The modified polyisocyanate of claim 59 wherein the mono- or di-lower alkyl dicyclopentadienyl iron compound is selected from the group consisting of ethyldicyclopentadienyl iron, n-butyldicyclopentadienyl iron, and diethyldicyclopentadienyl iron.

61. The modified polyisocyanate of claim 59 wherein the dimer or polymeric product is selected from the group consisting of 2,2-di(ethyldicyclopentadienyl iron)-propane, di(butylcyclopentadienyl iron)-propane, and di(cyclopentadienyl iron)-methane.

62. The modified polyisocyanate of claim 57 wherein the ferrocene compound is present in the reaction mixture in an amount ranging from about 0.05% to about 0.4% by weight of the amount of the original polyisocyanate.

63. The modified polyisocyanate of claim 62 wherein the ferrocene compound is present in an amount ranging from about 0.08% to about 0.3% by weight of the amount of the original polyisocyanate.

64. The modified polyisocyanate of claim 1 wherein an acidic compound is added to the reaction mixture to stop the isocyanuration of isocyanate groups.

65. The modified polyisocyanate of claim 64 wherein the acidic compound is selected from the group consisting of hydrochloric acid, phosphoric acid, dimethyl phosphate, trimethyl phosphate, triethyl phosphate, tricresyl phosphate, triphenyl phosphate, tributyl phosphate, p-toluenesulfonic acid, methyl p-toluenesulfonate, xylenesulfonic acid, benzenesulfonic acid, methanesulfonic acid, alkylbenzenesulfonic acids, dinaphthalenedisulfonic acid, dinaphthalenemonosulfonic acid, dinonylnaphthalenedisulfonic acid, dinonylnaphthalenemonosulfonic acid, benzoyl chloride, and acetyl chloride.

66. The modified polyisocyanate of claim 64 wherein the acidic compound is added to the reaction mixture in an amount ranging from about 0.3 to about 5.0 equivalents, based on the amount of trimerization catalyst present in the reaction mixture.

67. The modified polyisocyanate of claim 66 wherein the acidic compound is added in an amount ranging from about 1.0 to about 2.0 equivalents, based on the amount of trimerization catalyst present in the reaction mixture.

68. The modified polyisocyanate of claim 1 wherein the isocyanuration reaction is conducted at a temperature of not more than about 100° C.

69. The modified polyisocyanate of claim 68 wherein the isocyanuration reaction is conducted at a temperature of from about 15° C. to about 70° C.

70. A resin composition for polyisocyanurate foam comprising the modified polyisocyanate of claim 1, a polyol having a molecular weight of not less than about 200, a blowing agent, a catalyst, and a foam stabilizer.

71. the resin composition of claim 70 wherein the modified polyisocyanate is a modified polymethylenepolyphenyl polyisocyanate.

72. A polyisocyanurate foam produced from the resin composition of claim 70.

73. A polyisocyanurate foam produced from the resin composition of claim 71.

74. The foam of claim 72 wherein the polyol is selected from the group consisting of polyester polyols, polyether polyols, and mixtures thereof.

75. The foam of claim 74 wherein the polyester polyol is prepared from the reaction of a compound having at least two hydroxyl groups with a compound having at least two carboxyl groups.

76. The foam of claim 75 wherein the compound having at least two hydroxyl groups is selected from the group consisting of ethylene glycol, diethylene glycol, trimethylene glycol, 1,2-propylene glycol, 1,3-butanediol, tetramethylene glycol, hexamethylene glycol, decamethylene glycol, glycerin, trimethylolpropane, pentaerythritol, sorbitol, bisphenol A, and mixtures thereof.

77. The foam of claim 75 wherein the compound having at least two carboxyl groups is selected from the group consisting of malonic acid, maleic acid, succinic acid, adipic acid, tartaric acid, pimelic acid, sebacic acid, oxalic acid, phthalic acid, terephthalic acid, azelaic acid, trimellitic acid, glutaconic acid, α-hydromuconic acid, β-hydromuconic acid, α-butyl-α-ethylglutaric acid, α,β-diethylsuccinic acid, hemimellitic acid, 1,4-cyclohexanedicarboxylic acid, and mixtures thereof.

78. The foam of claim 74 wherein the polyester polyol is prepared from the transesterification reaction of a low-molecular-weight diol and a polyalkylene terephthalate polymer represented by the general formula

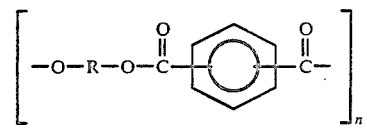

wherein R is an alkyl group having from 1 to 10 carbons, and wherein n is a whole number such that the molecular weight of the polyalkylene terephthalate polymer is at least 1500.

79. The foam of claim 78 wherein the low-molecular-weight diol is selected from the group consisting of ethylene glycol, propylene glycol, diethylene glycol, triethylene glycol, dipropylene glycol, butanediol, glycerol, trimethylolpropane, and mixtures thereof.

80. The foam of claim 74 wherein the polyether polyol is prepared from the addition-polymerization reaction of a monomer with an initiator, the initiator having at least two active hydrogen atoms.

81. The foam of claim 80 wherein the monomer is selected from the group consisting of ethylene oxide, propylene oxide, butylene oxide, amylene oxide, glycidyl ether, methyl glycidyl ether, t-butyl glycidyl ether, phenyl glycidyl ether, and mixtures thereof.

82. The foam of claim 80 wherein the initiator is selected from the group consisting of ethylene glycol, 1,3-propylene glycol, 1,2-propylene glycol, 1,4-butanediol, 1,3-butanediol, 1,2-butanediol, 1,5-pentanediol, 1,7-heptanediol, glycerin, trimethylolpropane, trimethylolethane, hexane-1,2,6 triol, α-methylglycoside, pentaerythritol, sorbitol, sucrose, glucose, fructose, bisphenol A, ethylenediamine, propylenediamine, diethylenetriamine, toluenediamine, metaphenylenediamine, diphenylmethanediamine, xylenediamine, and mixtures thereof.

83. The foam of claim 72 wherein the blowing agent is selected from the group consisting of trichloromonofluoromethane, dichlorodifluoromethane, dichloromonofluoromethane, dichlorotetrafluoroethane, trichlorotrifluoroethane, dibromotetrafluoroethane, methylene chloride, trichloroethane, benzene, toluene, pentane, hexane, water crystal-water-containing compounds, aldoximes, sodium bicarbonate, azoisobutylonitrile, ammonium carbonate, and mixtures thereof.

84. The foam of claim 83 wherein the blowing agent is trichloromonofluoromethane or water.

85. The foam of claim 72 wherein the catalyst is selected from the group consisting of alkali metal salts of carboxylic acids having from 2 to 12 carbons, amines, alcoholates, phenolates, and mixtures thereof.

86. The foam of claim 85 wherein the catalyst is selected from the group consisting of potassium acetate, potassium benzoate, potassium 2-ethylhexanate, potassium naphthenate, 2,4,6-tris(dimethylaminomethyl)phenol, triethylamine, N,N',N"tris(dimethylaminopropyl)hexahydrotriazine, triethylenediamine, diazabicycloundecene, tetramethylhexanediamine, potassium phenolate, and sodium methoxide.

87. The foam of claim 72 wherein the catalyst is present in an amount ranging from about 0.01% to about 20% by weight of the amount of the modified polyisocyanate.

88. The foam of claim 72 wherein the foam stabilizer is selected from the group consisting of silicone type surfactants, cation type surfactants, anion type surfactants, nonion type surfactants, and mixtures thereof.

89. The foam of claim 88 wherein the silicone type surfactant is selected from the group consisting of organopolysiloxanes, organopolysiloxane-polyoxyalkylene copolymers, and polyalkenylsiloxanes having a polyoxyalkylene side chain.

90. The foam of claim 72 wherein the resin composition further comprises an additive selected from the group consisting of fillers, flame retardants, and mixtures thereof.

91. The foam of claim 73 wherein the ratio of isocyanate groups to hydroxyl groups in the resin composition is not less than 2.0.

92. A process for producing a polyisocyanurate foam by the foaming reaction of a resin composition comprising a polyol having a molecular weight of not less than about 200, a blowing agent, a catalyst, a foam stabilizer, and a modified polyisocyanate containing an isocyanurate ring, wherein the modified polyisocyanate is produced from the reaction of an original polyisocyanate selected from the group consisting of organic polyisocyanates, partially urethanized organic polyisocyanates, and mixtures thereof, in a reaction mixture comprising a trimerization catalyst, an organic phosphite ester, and a surfactant, to cause isocyanuration of not more than about 20% by weight of the isocyanate groups in the original polyisocyanate, wherein the constituents of the resin composition are mixed homogeneously before foaming.

93. The process of claim 92 wherein the modified polyisocyanate is a modified polymethylenepolyphenyl polyisocyanate.

* * * * *

UNITED STATES PATENT AND TRADEMARK OFFICE
CERTIFICATE OF CORRECTION

PATENT NO. : 5,102,918
DATED : April 7, 1992
INVENTOR(S) : KIOYOSHI Moriya

Page 1 of 2

It is certified that error appears in the above-indentified patent and that said Letters Patent is hereby corrected as shown below:

On the title page: Item [56]

In the title listed for Attorney, Agent or Firm, change "Hoixe" to --Hoxie--.

In the Abstract, at line 3, delete "estr" and insert --ester--.

Column 1, line 7, delete "isocyauurate" and insert --isocyanurate--.

Column 3, line 53, delete "2,4-" and insert --2,4'--.

Column 7, line 41, change "100°C." to --100°C--.

Column 8, line 36, delete "tripheryl" and insert --triphenyl--.

UNITED STATES PATENT AND TRADEMARK OFFICE
CERTIFICATE OF CORRECTION

PATENT NO. : 5,102,918
DATED : April 7, 1992
INVENTOR(S) : Kioyoshi Moriya

It is certified that error appears in the above-indentified patent and that said Letters Patent is hereby corrected as shown below:

Column 17, line 35, change "28 4%" to --28.4%--.

Claim 4, column 31, lines 19-20, delete "of from about 60°C. to about 90°C." and insert --of not more than about 100°C.--

Claim 22, column 32, line 45, delete "on combustible", and insert --incombustible--.

Claim 37, column 33, line 34, delete "pentraerythrityl" and insert --pentaerythrityl--.

Claim 63, column 35, line 43, delete "a n", and add --an--.

Signed and Sealed this

Twenty-sixth Day of October, 1993

BRUCE LEHMAN

Attesting Officer    Commissioner of Patents and Trademarks